(12) United States Patent
Nabbe et al.

(10) Patent No.: US 10,328,897 B1
(45) Date of Patent: Jun. 25, 2019

(54) AUTHORIZED REMOTE CONTROL

(71) Applicant: Apple Inc., Cupertino, CA (US)

(72) Inventors: Bartholomeus C. Nabbe, Redwood City, CA (US); Tie-Qi Chen, Cupertino, CA (US); Benjamin B. Lyon, Saratoga, CA (US)

(73) Assignee: Apple Inc., Cupertino, CA (US)

( * ) Notice: Subject to any disclaimer, the term of this patent is extended or adjusted under 35 U.S.C. 154(b) by 5 days.

(21) Appl. No.: 15/275,147

(22) Filed: Sep. 23, 2016

Related U.S. Application Data

(60) Provisional application No. 62/232,781, filed on Sep. 25, 2015.

(51) Int. Cl.
*B60R 25/20* (2013.01)
*G05D 1/00* (2006.01)
*G01C 21/26* (2006.01)
*G06F 21/30* (2013.01)
*B60R 99/00* (2009.01)
(Continued)

(52) U.S. Cl.
CPC .......... *B60R 25/2018* (2013.01); *G01C 21/26* (2013.01); *G05D 1/0011* (2013.01); *G06F 21/305* (2013.01); *A61B 5/18* (2013.01); *B60R 99/00* (2013.01); *G05D 1/0022* (2013.01); *G06Q 10/06* (2013.01); *G07C 5/00* (2013.01); *G07C 5/008* (2013.01)

(58) Field of Classification Search
CPC ....... G08B 23/00; G08B 21/02; B60W 40/08; G08G 1/096725; G08G 1/0967; G08G 1/0133; G08G 1/0145; G08G 1/20; G08G 1/00; G08G 1/01; G08G 1/052; G05D 1/02; G05D 1/0297; G05D 1/0011; G05D 1/0022; H04W 4/046; H04W 4/027; H04W 4/02; H04W 4/04; H04L 63/0428; H04L 9/32; H04L 29/06; H04L 9/14; H04L 9/30; B60R 25/2018; B60R 99/00; G01C 21/26; G06F 21/305; G06Q 10/06; G06Q 10/06398; G07C 5/00; G07C 5/008; B60K 28/06
See application file for complete search history.

(56) References Cited

U.S. PATENT DOCUMENTS 8,725,311 B1   5/2014   Breed
8,874,301 B1   10/2014  Rao et al.
(Continued)

*Primary Examiner* — Behrang Badii
(74) *Attorney, Agent, or Firm* — Richard C. Kowert; Meyertons, Hood, Kivlin, Kowert & Goetzel, P.C.

(57) ABSTRACT

Some embodiments provide a vehicle navigation system which can navigate a vehicle through an environment based on driving commands received from a remote control system based on manual operator interaction with an interface of the remote control system. Remote driving control can be engaged based on determination, via processing vehicle sensor data, of a health emergency associated with one or more occupants of the vehicle, and the remote control system can generate remote driving commands which cause the vehicle to be navigated to a particular location without requiring the occupant associated with the health emergency to manually navigate the vehicle. The remote control system can monitor the occupant via communicated vehicle sensor data and can control remote control devices included in the vehicle to provide external indication that the vehicle is being navigated according to remote driving control.

21 Claims, 9 Drawing Sheets

(51) Int. Cl.
    *A61B 5/18*     (2006.01)
    *G07C 5/00*     (2006.01)
    *G06Q 10/06*    (2012.01)

(56) References Cited

U.S. PATENT DOCUMENTS

| | | | |
|---|---|---|---|
| 9,988,055 B1* | 6/2018 | O'Flaherty | H04W 4/90 |
| 2003/0221118 A1* | 11/2003 | Walker | B60R 25/042 |
| | | | 713/193 |
| 2010/0030434 A1 | 2/2010 | Okabe et al. | |
| 2012/0123644 A1* | 5/2012 | Waldmann | B60T 7/042 |
| | | | 701/45 |
| 2013/0179024 A1* | 7/2013 | Nordbruch | A61B 5/18 |
| | | | 701/23 |
| 2014/0143839 A1 | 5/2014 | Ricci | |
| 2014/0207535 A1* | 7/2014 | Stefan | G05D 1/0022 |
| | | | 705/7.42 |
| 2016/0071418 A1* | 3/2016 | Oshida | G08G 1/22 |
| | | | 701/23 |
| 2017/0243484 A1* | 8/2017 | Li | G08G 1/096716 |

* cited by examiner

AUTHORIZED REMOTE CONTROL

This application claims benefit of priority of U.S. Provisional Application Ser. No. 62/232,781, filed Sep. 25, 2015, which is hereby incorporated by reference herein in its entirety.

BACKGROUND

Technical Field

This disclosure relates generally to navigation of a vehicle, and in particular to remotely-controlled driving control of the vehicle via a remote control system communicatively coupled to a navigation system of the vehicle via a communication network.

Description of the Related Art

The rise of interest in autonomous navigation of vehicles, including automobiles, has resulted in a desire to develop autonomous navigation systems which can autonomously navigate (i.e., autonomously "drive") a vehicle through various routes, including one or more roads in a road network, such as contemporary roads, streets, highways, etc. Such autonomous navigation systems can control one or more automotive control elements of the vehicle to implement such autonomous navigation. Such control by the autonomous navigation system in a vehicle can be referred to as autonomous driving control of the vehicle.

Vehicles which include autonomous navigation systems may enable one or more occupants to manually control one or more vehicle control elements of the vehicle, such that one or more occupants of the vehicle can manually navigate ("drive") the vehicle. Such control by an occupant can be referred to as manual driving control of the vehicle.

SUMMARY OF EMBODIMENTS

Some embodiments provide a vehicle navigation system which can navigate a vehicle through an environment based on driving commands received from a remote control system based on manual operator interaction with an interface of the remote control system. Remote driving control can be engaged based on determination, via processing vehicle sensor data, of a health emergency associated with one or more occupants of the vehicle, and the remote control system can generate remote driving commands which cause the vehicle to be navigated to a particular location without requiring the occupant associated with the health emergency to manually navigate the vehicle. The remote control system can monitor the occupant via communicated vehicle sensor data and can control remote control devices included in the vehicle to provide external indication that the vehicle is being navigated according to remote driving control.

Some embodiments provide an apparatus which includes a vehicle navigation system configured to be installed in a vehicle and navigate the vehicle through an environment in which the vehicle is located based on remote driving commands received from a remote control system. The vehicle navigation system is configured to: generate a remote control request signal, to the remote control system, based at least in part upon a determination that an occupant of an interior of the vehicle is associated with an emergency health state.

Some embodiments provide an apparatus which includes a remote control system, remotely located from a vehicle, which is configured to selectively engage in remote driving control of the vehicle. The remote control system is configured to generate a set of remote driving commands which, when executed at a vehicle navigation system of the vehicle, cause the vehicle to be navigated through an environment, based at least in part upon a determination that remote driving control of the vehicle is authorized by one or more of the vehicle or an authorized end user supported by a separate user device.

Figure 1:
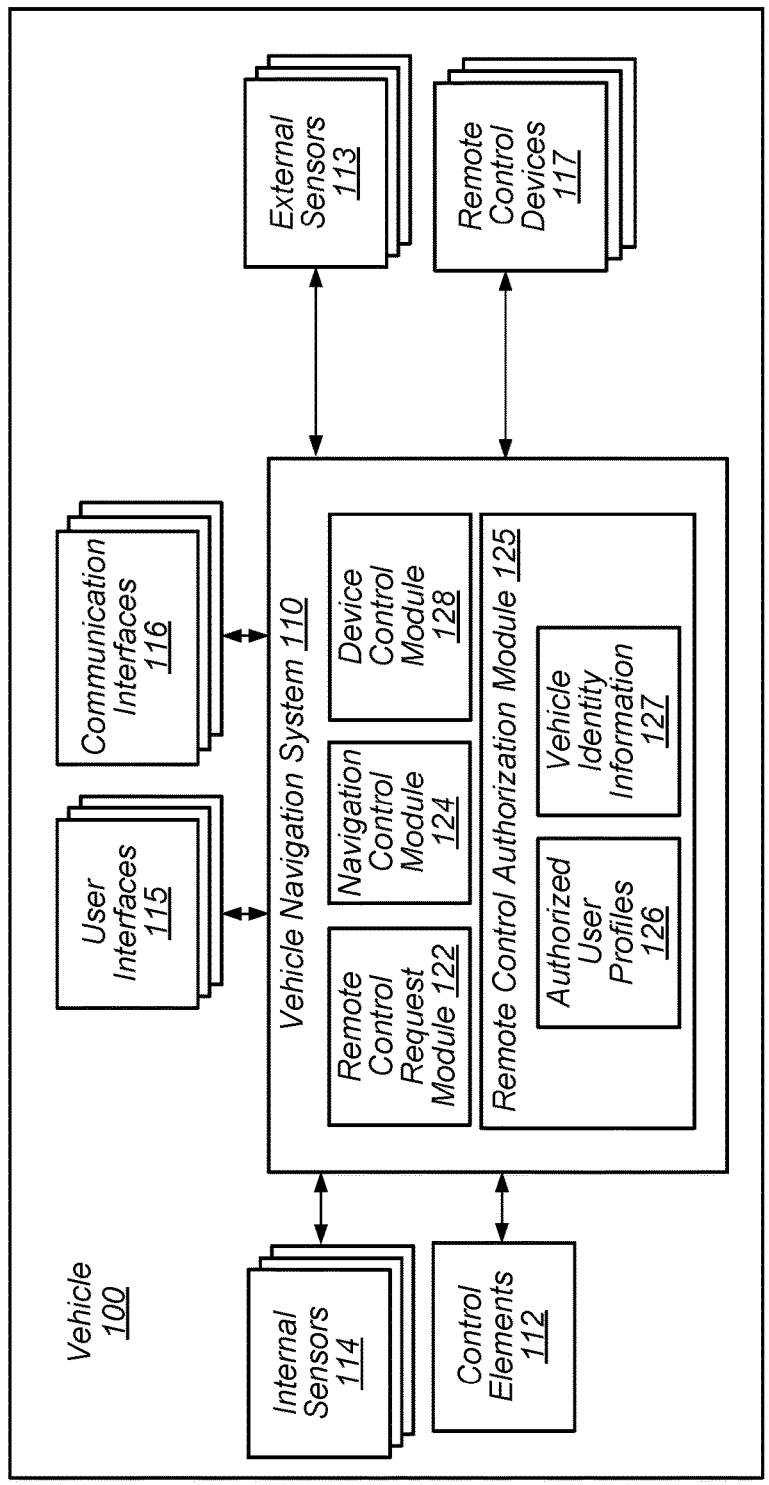
FIG. 1 illustrates a schematic block diagram of a vehicle 100 which comprises a vehicle navigation system (VNS), according to some embodiments.

This specification includes references to "one embodiment" or "an embodiment." The appearances of the phrases "in one embodiment" or "in an embodiment" do not necessarily refer to the same embodiment. Particular features, structures, or characteristics may be combined in any suitable manner consistent with this disclosure.

"Comprising." This term is open-ended. As used in the appended claims, this term does not foreclose additional structure or steps. Consider a claim that recites: "An apparatus comprising one or more processor units . . . ." Such a claim does not foreclose the apparatus from including additional components (e.g., a network interface unit, graphics circuitry, etc.).

"Configured To." Various units, circuits, or other components may be described or claimed as "configured to" perform a task or tasks. In such contexts, "configured to" is used to connote structure by indicating that the units/circuits/components include structure (e.g., circuitry) that performs those task or tasks during operation. As such, the unit/circuit/component can be said to be configured to perform the task even when the specified unit/circuit/component is not currently operational (e.g., is not on). The units/circuits/components used with the "configured to" language include hardware—for example, circuits, memory storing program instructions executable to implement the operation, etc. Reciting that a unit/circuit/component is "configured to" perform one or more tasks is expressly intended not to invoke 35 U.S.C. § 112, sixth paragraph, for that unit/circuit/component. Additionally, "configured to" can include generic structure (e.g., generic circuitry) that is manipulated by software and/or firmware (e.g., an FPGA or a general-purpose processor executing software) to operate in manner that is capable of performing the task(s) at issue. "Configure to" may also include adapting a manufacturing process (e.g., a semiconductor fabrication facility) to fabricate devices (e.g., integrated circuits) that are adapted to implement or perform one or more tasks.

"First," "Second," etc. As used herein, these terms are used as labels for nouns that they precede, and do not imply any type of ordering (e.g., spatial, temporal, logical, etc.). For example, a buffer circuit may be described herein as performing write operations for "first" and "second" values. The terms "first" and "second" do not necessarily imply that the first value must be written before the second value.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While in this case, B is a factor that affects the determination of A, such a phrase does not foreclose the determination of A from also being based on C. In other instances, A may be determined based solely on B.

DETAILED DESCRIPTION

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that some embodiments may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first contact could be termed a second contact, and, similarly, a second contact could be termed a first contact, without departing from the intended scope. The first contact and the second contact are both contacts, but they are not the same contact.

The terminology used in the description herein is for the purpose of describing particular embodiments only and is not intended to be limiting. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

FIG. 1 illustrates a schematic block diagram of a vehicle 100 which comprises a vehicle navigation system (VNS) which is configured to control various control elements of the vehicle to navigate the vehicle through an environment, according to some embodiments. The VNS can control various control elements based on driving control commands generated at one or more user interfaces, navigation control modules, remote control systems, etc. The VNS, in some embodiments, includes an autonomous navigation system (ANS) which is configured to autonomously generate autonomous driving control commands which control various control elements of the vehicle to autonomously navigate the vehicle along one or more driving routes.

Vehicle 100 will be understood to encompass one or more vehicles of one or more various configurations which can accommodate one or more occupants, including, without limitation, one or more automobiles, trucks, vans, etc. Vehicle 100 can include one or more interior cabins ("vehicle interiors") configured to accommodate one or more human occupants (e.g., passengers, drivers, etc.), which are collectively referred to herein as vehicle "occupants". A vehicle interior can include one or more user interfaces 115, including one or more manual driving control interfaces (e.g., steering device, throttle control device, brake control device), display interfaces, multimedia interfaces, climate control interfaces, some combination thereof, or the like.

Vehicle 100 includes various vehicle control elements 112 which can be controlled, via one or more of the interfaces 115 and the VNS 110, to navigate ("drive") the vehicle 100 through the world, including navigate the vehicle 100 along one or more driving routes. In some embodiments, one or more control elements 112 are communicatively coupled to one or more user interfaces 115 included in the vehicle 100 interior, such that the vehicle 100 is configured to enable an occupant to interact with one or more user interfaces 115, including one or more manual driving control interfaces, to control at least some of the control elements 112 and manually navigate the vehicle 100 via manual driving control of the vehicle via the manual driving control interfaces 115. For example, vehicle 100 can include, in the vehicle interior, a steering device, throttle device, and brake device which can be interacted with by an occupant to control various control elements 112 to manually navigate the vehicle 100.

Vehicle 100 includes a vehicle navigation system (VNS) 110 which is configured to generate control element commands which cause the vehicle 100 to be navigated though an environment. In some embodiments, a VNS is implemented by one or more computer systems. VNS 110 is communicatively coupled to at least some of the control elements 112 of the vehicle 100 and is configured to control one or more of the elements 112 to navigate the vehicle 100. Control of the one or more elements 112 to autonomously navigate the vehicle 100 can include VNS 110 generating one or more control element commands, also referred to herein interchangeably as control element signals.

In some embodiments, VNS 110 generates control element signals which cause one or more sets of control elements 112 to navigate the vehicle 100 through the environment based on input received at VNS 110 via one or more user interfaces 115. Such generation of control element signals can also referred to as manual driving control of the vehicle 100 at the VNS 110.

In some embodiments, VNS 110 autonomously generates control element signals which cause one or more sets of control elements 112 to navigate the vehicle 100 through the environment along a particular driving route. Such control can also referred to as autonomous driving control of the vehicle 100 at the VNS 110. As used herein, autonomous navigation of the vehicle 100 refers to controlled navigation ("driving") of vehicle 100 along at least a portion of a route based upon autonomous driving control, by VNS 110, of the control elements 112 of the vehicle 100, including steering control elements, throttle control elements, braking control elements, transmission control elements, etc. independently of manual driving control input commands receiving from a user of the vehicle via user interaction with one or more user interfaces 115.

Vehicle 100 includes one or more communication interfaces 116 which are communicatively coupled with VNS 110 and are configured to communicatively couple VNS 110 to one or more remotely located systems, services, devices, etc. via one or more communication networks. For example, an interface 116 can include one or more cellular communication devices, wireless communication transceivers, radio communication interfaces, etc. VNS 110 can be communicatively coupled, via an interface 116, with one or more remote services via one or more wireless communication networks, including a cloud service. VNS 110 can communicate messages to a remote service, system, etc., receive messages from the one or more remote services, systems, etc., and the like via one or more interfaces 116. In some embodiments, communicatively coupling VNS 110 with a remote service, system, etc. via interface 116 includes establishing a two-way communication link between the VNS 110 and the remote service, system, etc. via a communication network to which the interface 116 is communicatively coupled.

Vehicle 100 includes a set of one or more external sensor devices 113, also referred to as external sensors 113, which can monitor one or more aspects of an external environment relative to the vehicle 100. Such sensors can include camera devices, video recording devices, infrared sensor devices, radar devices, depth camera devices which can include one or more light-scanning devices including LIDAR devices, precipitation sensor devices, ambient wind sensor devices, ambient temperature sensor devices, position-monitoring devices which can include one or more global navigation satellite system devices (e.g., GPS, BeiDou, DORIS, Galileo, GLONASS, etc.), some combination thereof, or the like. One or more of external sensor devices 113 can generate sensor data associated with an environment as the vehicle 100 navigates through the environment. Sensor data generated by one or more sensor devices 113 can be communicated to VNS 110 as input data, where the input data can be used by the VNS 100, when operating in autonomous driving control mode, to generate driving control signals which, when executed by control elements 112, cause the vehicle 100 to be navigated along a particular driving route through the environment. In some embodiments, VNS 110 communicates at least some sensor data generated by one or more sensors 113 to one or more remote systems, services, etc. via one or more interfaces 116.

Vehicle 100 includes a set of one or more internal sensors 114, also referred to as sensor devices 114, which can monitor one or more aspects of the vehicle 100 interior. Such sensors can include camera devices, including one or more visible light cameras, infrared cameras, near-infrared cameras, depth cameras which can include one or more light-scanning devices including LIDAR devices, some combination thereof, etc. configured to collect image data of one or more occupants in the vehicle interior, control element sensors which monitor operating states of various driving control interfaces 115 of the vehicle, chemical sensors which monitor the atmosphere of the vehicle interior for the presence of one or more chemical substances, some combination thereof, etc. One or more of internal sensor devices 114 can generate sensor data. Sensor data generated by one or more internal sensor devices 114 can be communicated to VNS 110, where the input data can be used by the VNS 110 to determine a health state of one or more occupants of the vehicle 100 interior. In some embodiments, one or more sensors 114 generate sensor data regarding one or more particular positions within the vehicle interior, and sensor data generated by the sensors 114 can be used by the VNS to determine whether one or more occupants located in one or more particular positions in the vehicle interior is associated with an emergency health state. The VNS 110 can continuously monitor the health state parameters associated with occupants of the vehicle interior. In some embodiments, VNS 110 is configured to monitor health state parameters of human individuals located external to the vehicle within a certain proximity distance of the vehicle, based on processing sensor data generated by one or more sensor devices 113.

The sensors 114 can generate data which can be processed by VNS 110 to determine one or more parameters associated with the occupant's health, including occupant pupil dilation, blinking body temperature, heartbeat, perspiration, head position, etc. Such parameters can be referred to as health state parameters of the occupant. VNS 110 can process the parameters and determine a "health state" of the occupant, including a "drowsy state", "intoxicated state", cognitively impaired state", "emergency health state", etc., based on comparing one or more of the health state parameters against one or more health state parameter threshold values associated with the one or more particular health states.

VNS 110 includes a set of modules which are configured to enable VNS 110 to cause the vehicle 100 to be navigated through an environment based on remote driving control of the vehicle. Remote driving control can be based on one or more remote driving command signals, also referred to herein as remote driving commands, received at VNS 110 from one or more remote control systems via one or more interfaces 116.

VNS 110 includes an remote control request module 122 which determines whether to generate a remote control request signal which, when received at a remotely located remote control system, is processed as a request, by VNS 110, for the remote control system to engage remote driving control of the VNS 110 via one or more interfaces 116.

Module 122 can monitor one or more aspects of the interior and exterior of the vehicle, via sensor data generated by one or more sensors 113-114, and can determine whether to generate a remote control request signal which is transmitted to a remote control system via an interface 116 based on monitoring one or more health state parameters associated with one or more occupants of the vehicle interior, proximate external individuals, etc. For example, module 122 can monitor a health state of an occupant of the vehicle interior, via sensor data generated by a sensor 114, and can generate a remote control request message based on a determination that the health state of the occupant corresponds to an emergency health state. The remote control request message can include information specifying a basis upon which module 122 generates the message, including a specification of a health state of an occupant of the vehicle. In some embodiments, the remote control request signal includes an emergency remote control signal, generated based at least in part upon the deterring that a health state of an occupant of the vehicle 100 corresponds with an emergency health state, which includes a request for a remote control system to remotely control vehicle 100 so that vehicle 100 is remotely navigated to a medical care location, including an emergency care center, hospital, etc. In some embodiments, the remote control request signal includes health state parameter data associated with a monitored vehicle occupant, proximate external individual, etc.

In some embodiments, module 122 generates a remote control request signal based on user-initiated commands received at VNS 110 from an interface 115. For example, an interface 115 can include a remote control element with which a user can interact to command module 122 to generate a remote control request, to a remote control system via an interface 116, to engage in remote control of the vehicle 100. In some embodiments, module 122 generates a remote control request signal based on user-initiated commands received at VNS 110 from a user device which is separate from vehicle 100. In some embodiments, module 122 generates a remote control request based on determining that user information included in the user-initiated commands received at VNS 110 from a user device identifies a user profile which is associated, at module 125, with a set 126 of authorized users.

VNS 110 can include a navigation control module 124 which is configured to generate control element signals which are executed by one or more control elements 112 to cause the vehicle 100 to be navigated. Module 124 is configured to establish a driving control mode of the VNS 110 and generate control element signal based on the present driving control mode of the VNS 110. The driving control mode can include one or more of a manual driving control mode, autonomous driving control mode, and a remote driving control mode. In some embodiments, module 124 processes particular inputs to VNS 110 based on the present driving control mode of VNS 110. For example, where VNS 110 is in a manual driving control mode, module 124 can selectively generate control element signals based on manual driving control commands received at VNS 110 via one or more user interfaces 115. In another example, where VNS 110 is in an autonomous driving control mode, module 124 can generate control signals based on processing sensor data generated by one or more sensors 113 and a driving route along which the vehicle 100 is to be navigated, where module 124 can switch between autonomous driving control mode and manual driving control mode based on signals received from one or more interfaces 115. The driving route can be generated at module 124 based on input commands received from an interface 115, data received from one or more interfaces 116, etc. In another example, where VNS 110 is in a remote driving control mode, module 124 can generate control signals based on remote control commands received from a remote control system via one or more interfaces 116. Where VNS 110 is in a remote driving control mode, module 124 can selectively ignore driving control commands received at VNS 110 from one or more interfaces 115.

Module 124 can switch the VNS 110 to a remote driving control mode based on one or more of generation of an remote control request signal at module 122, receipt of one or more remote driving commands from a remote control system via an interface 116, generation of an authorization signal at module 125, receipt of an authorization confirmation signal from a remote control system via an interface 116, some combination thereof, etc.

In some embodiments, module 124 selectively switches the VNS 110 between remote driving control mode and one or more other driving control modes based on a remote control switching command received at VNS 110 from a remote control system via one or more interfaces 116. A remote control switch command can include authorization information which identifies the remote control system and includes password information which is processed by module 125 to determine that remote control driving mode is authorized and confirmed at the remote control system.

VNS 110 includes an authorization module 125 which selectively authorizes remote driving control of VNS 110 at a remote control system. Module 125 includes one or more of vehicle identity information 127 which uniquely identifies the vehicle 100, user profile information 126 which uniquely identifies particular user profiles associated with one or more end users which are authorized to command remote driving control of VNS 110, etc.

Users can benefit from use of personal data, which can include user profile information 126 associated with a user profile. For example, the personal data can be used to ensure that remote control of a vehicle is authorized by particular users. Accordingly, use of such personal data enables users to influence and control whether remote driving control of a vehicle is engaged. In some embodiments, the personal data can include health data associated with an occupant which can be, based on authorization by the occupant, transmitted to one or more remote systems, services, etc., including the remote control system, a remote medical service, a remote medical facility, etc., and the personal data can be used to determine a destination, including a particular medical center, to which the vehicle is remotely navigated. As a result, the personal data can be used to enable an occupant in medical distress to be navigated to an appropriate location where the occupant can receive care tailored to the occupant's health state.

Users, which can include occupants, can selectively block use of, or access to, personal data. A system incorporating some or all of the technologies described herein can include hardware and/or software that prevents or blocks access to such personal data. For example, the system can allow users to "opt in" or "opt out" of participation in the collection of personal data or portions of portions thereof. Also, users can select not to provide location information, or permit provision of general location information (e.g., a geographic region or zone), but not precise location information.

Entities responsible for the collection, analysis, disclosure, transfer, storage, or other use of such personal data should comply with established privacy policies and/or practices. Such entities should safeguard and secure access to such personal data and ensure that others with access to the personal data also comply. Such entities should implement privacy policies and practices that meet or exceed industry or governmental requirements for maintaining the privacy and security of personal data. For example, an entity should collect users' personal data for legitimate and reasonable uses, and not share or sell the data outside of those legitimate uses. Such collection should occur only after receiving the users' informed consent. Furthermore, third parties can evaluate these entities to certify their adherence to established privacy policies and practices.

Module 125 can, in response to receipt of a remote control authorization request signal from a remote control system via an interface 116, determine whether to authorize the remote driving control of the VNS 110 at the remote control system based on processing information included in the request signal. Based on determining that the request is to be authorized, module 125 can generate an authorization signal which authorizes the remote control system to remotely control the vehicle 100. The module 125 can, based on determining that the request is to be authorized, command module 124 to switch to remote driving control mode, so that the module 124 is commanded to generate control element signals based on remote driving commands received at VNS 110 from the remote control system via an interface 116.

In some embodiments, module 125 determines whether to authorize remote driving control of vehicle 100 based on comparing data included in the authorization request with one or more sets of data. In some embodiments, where VNS 110 receives a remote control authorization request signal which indicates that remote control of vehicle 100 is requested by a user, separately from generation of a remote control request signal at module 122, the authorization request signal can include information identifying a user profile associated with the user requesting that remote driving control of VNS 110 be engaged. Module 125 can compare the user identifying information with a stored set 126 of user profiles which are determined to be associated with users who are authorized to request that remote control of VNS 110 be engaged. Upon determining that the user indicated in the authorization request correlates with an authorized user profile 126, module 125 can generate an authorization signal which indicates, to the remote control system, that VNS 110 authorizes remote control of vehicle 100 by the remote control system.

Where the authorization request signal includes vehicle identification data identifying a vehicle 100 for which remote control is requested, module 125 can compare the vehicle identification data to stored identify information 127 and can generate an authorization signal based on determining that the vehicle identification data include in the authorization request signal matches the vehicle identity information 127 associated with vehicle 100. Such information can include a password, passcode, key, etc. associated with "unlocking" remote driving control of the vehicle, so that module 125 can generate an authorization signal based on determining that the password, passcode, key, etc. is included in the authorization request signal.

Vehicle 110 includes a set of remote control devices 117 which are configured to be selectively activated and controlled based on VNS 110 operating in a remote driving control mode. The devices 117 can be configured to be inhibited, disabled, etc. when VNS 110 is in other driving control modes, including manual driving control mode, autonomous driving control mode, etc.

In some embodiments, devices 117 include one or more sets of devices which indicate, to one or more elements of an external environment in which the vehicle 100 is located, that the vehicle is being navigated through the environment based on remote control of the VNS 110. For example, devices 117 can include a set of light indicators, noisemakers, sirens, audio speaker devices, etc. The devices 117 can generate a predetermined set of signal patterns, including particular light signal patterns, audio signals, etc. In some embodiments, the devices 117, when activated, indicate that the vehicle 100 is being operated as an emergency vehicle and is to be considered by other external traffic participants to be an emergency vehicle. An emergency vehicle can include, for example, an ambulance. In some embodiments, one or more devices 117 include one or more particular interface devices which, when activated, can be controlled to actively interact with one or more elements of the external environment. For example, one or more devices 117 can include a traffic control device, including an infrared signaling device, which can control one or more traffic control signals in the environment. In some embodiments, one or more of the remote control devices 117 includes a speaker device via which audio commands, prompts, messages, etc. can be provided to one or more vehicle occupants, proximate external individuals, etc. The audio commands, prompts, messages, etc. can be predetermined messages generated at one or more of the VNS 110 or a remote control system, audio signals generated via operator interaction with an audio interface at the remote control system, etc. For example, an operator at the remote control system can utilize one or more remote control devices 117 to communicate with an occupant of the vehicle 100, communicate with a proximate external individual, etc. The operator may communicate with an occupant of the vehicle to request and provide information, request that the occupant perform certain acts, etc. The operator may communicate with a proximate external individual to request the individual to enter the vehicle interior.

VNS 110 includes a device control module 128 which is configured to selectively activate and control one or more of the remote control devices 117 based on determining that the module 124 has switched VNS 110 into a remote driving control mode. In some embodiments, module 128 selectively activates and controls one or more of the devices 117 based on one or more commands received from a remote control system via an interface 116. In some embodiments, module 128 disables some or all of devices 117, such that the devices are deactivated, based on determining that a remote driving control mode of VNS 110 is deactivated. Module 128 can inhibit control of devices 117 at vehicle based on user-initiated commands received from one or more interfaces 115, based on a determination that the remote driving control of VNS 110 is presently disabled.

Figure 2:
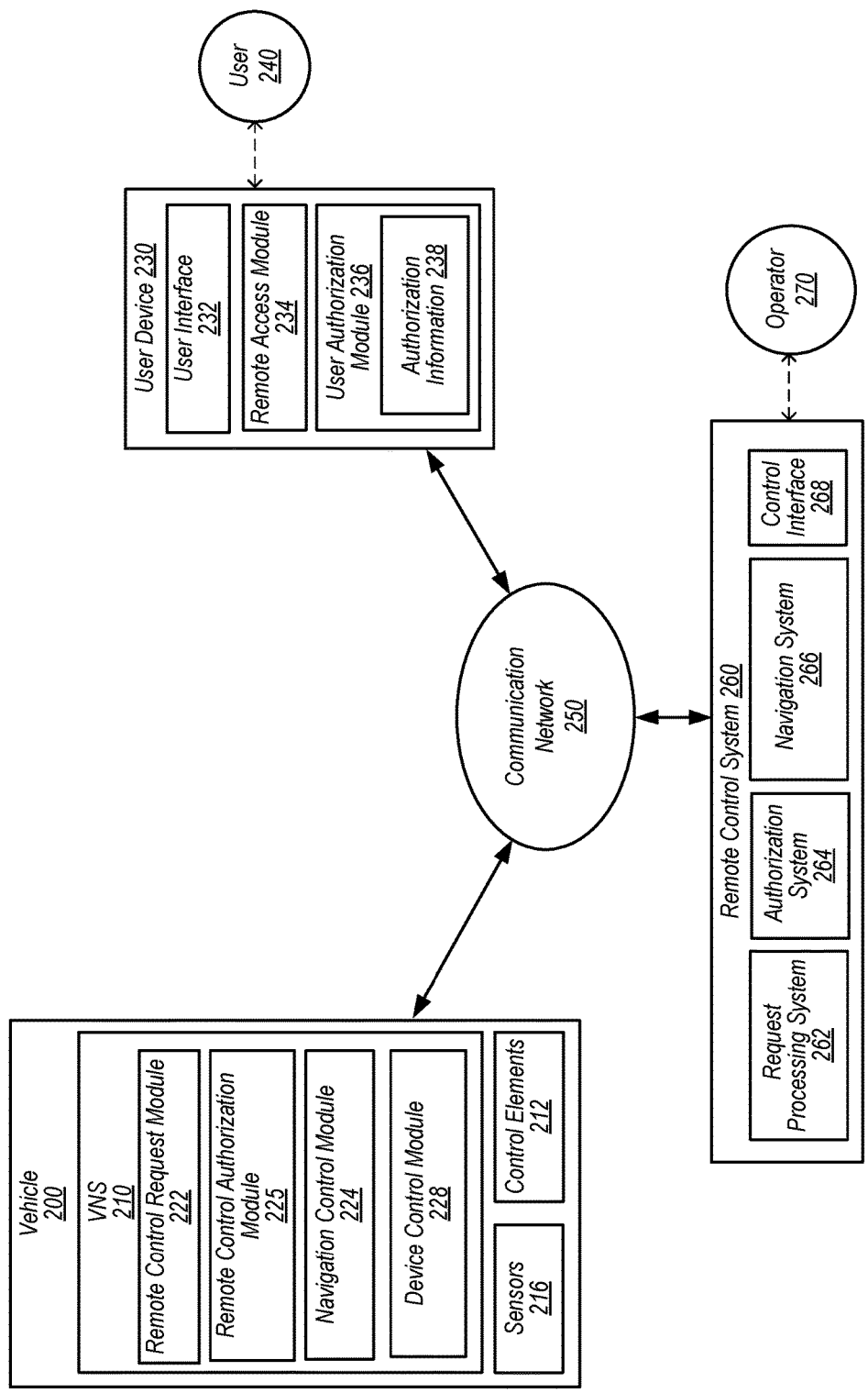
FIG. 2 illustrates a block diagram schematic of a vehicle and remote control system which are communicatively coupled via a communication network, according to some embodiments.
Figure 3:
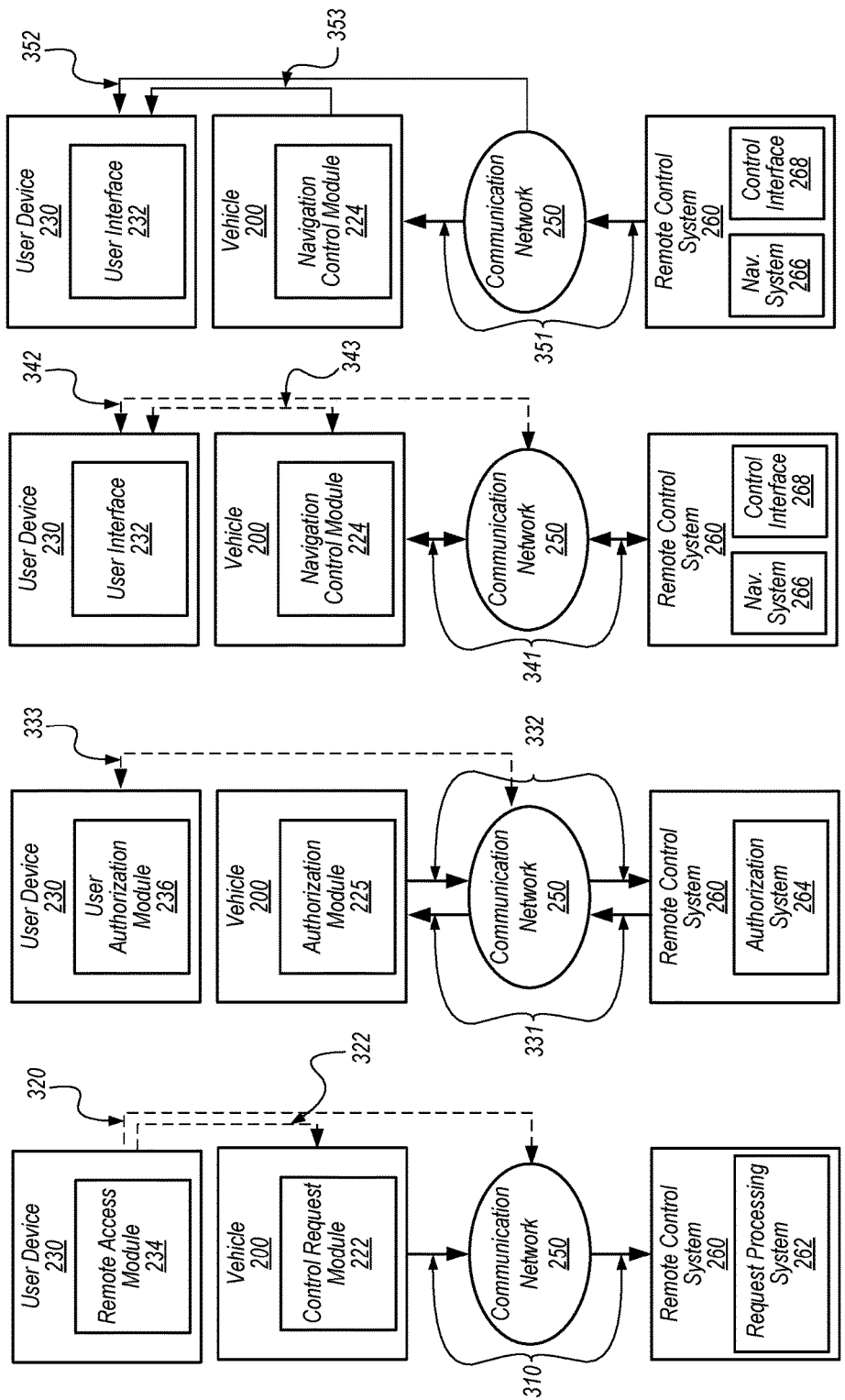
FIG. 3A-D illustrates interactions between the remote control system, a vehicle, and a user device associated with selectively engaging remote driving control of the vehicle at the remote control system, according to some embodiments.

FIG. 2 illustrates a block diagram schematic of a vehicle and remote control system which are communicatively coupled via a communication network, according to some embodiments. The vehicle 200 and VNS 210 illustrated in FIG. 2 can include any of the embodiments of vehicles and VNSs, etc. included herein, including vehicle 100 and VNS 210 illustrated and discussed with reference to FIG. 1. One or more of the VNS 210, remote control system 260, user device 230, etc. can be implemented by one or more computer systems.

FIG. 2 illustrates a remote control system 260 which is configured to enable selectively engaged remote driving control of a vehicle 200 via a communication network 250, where an operator 270 interacting with a control interface provided by the remote control system 260 can control the navigation of the vehicle 200 through one or more environments. As a result, remote control system 260 enables remote driving control of vehicle 200 based on interaction of operator 270 with one or more interfaces of system 260.

As shown, vehicle 200 includes a VNS 210. The VNS 210 includes a remote control request module 222 that is configured to generate a remote control request signal which includes a request for system 260 to engage remote driving control of vehicle 200. Module 222 can generate the signal based on determining that a health state of one or more individuals located in the vehicle 200 interior, proximate to the vehicle 200, some combination thereof, etc. correlates with an emergency health state. In some embodiments, an occupant of the vehicle 200 can interact with one or more interfaces of the vehicle 200 to command module 222 to generate the remote control request signal. Such interaction can include an occupant of the vehicle 200 commanding the module 222 to establish a communication link with one or more operators of the remote control system 260.

The remote control request signal can be communicated from vehicle 200 to system 260 via network 250. In some embodiments, the remote control request signal includes vehicle identity information identifying the vehicle 200, one or more instances of health state information associated with one or more individuals, occupants, etc., an indication of a basis upon which module 222 generates the request signal, some combination thereof, etc.

The remote control system 260 includes a request processing system 262 which is configured to determine, based on receipt of the remote control request signal, that remote driving control of vehicle 200 at system 260 is requested. System 262 can determine an identity of the vehicle 200, which can include contact address information which indicates a contact address of the vehicle via which system 260 can communicate with VNS 210 via network 250.

System 260 includes an authorization system 264 which is configured to generate a remote control authorization request signal, based on the determination at system 262 that remote driving control of vehicle 200 at system 260 is requested. The authorization request signal includes a request for authorization of remote driving control of the vehicle 220. System 260 can be configured to selectively engage remote driving control of vehicle 200 based on determination that remote driving control is authorized. The authorization request signal can be transmitted to vehicle 200 over network 250.

In some embodiments, the remote control system 260 is comprised in a civil emergency response system, sometimes referred to as a "911" emergency response service. In some embodiments, a user can establish a communication link can be established with one or more operators of the system 260 and can request the system 260 to establish remote driving control of the vehicle 200. Such a request can be communicated verbally via an audio communication link between a device supporting the user, including one or more of a user device 230, an interface included in the vehicle 200, etc.

VNS 210 includes an authorization module 225 which is configured to process an authorization request signal received from a remote control system 260 via network 250 and generate an authorization signal which indicates authorization of remote driving control of vehicle 200. In some embodiments, module 225 generates the authorization signal based on determining that one or more instances of user identity information, vehicle identity information, etc. included in the authorization request signal matches with one or more instances of authorized user identity information, vehicle identity information, etc. associated with the vehicle 200. For example, where authorization request signal generated at system 264 includes a remote control password, module 225 can compare the password with a stored instance of vehicle identity data which includes a remote control password associated with vehicle 200 and can determine, based on determining that the password included in the authorization request matches with the stored password, that the authorization request is proper. The module 225 can generate an authorization signal based on a determination that the authorization request is proper, where the authorization signal includes information indicating that remote driving control of the vehicle 200 is authorized.

As referred to herein, remote driving control of a vehicle can be referred to interchangeably as remote driving control of a VNS which is included in the vehicle.

In some embodiments, the authorization signal can include information indicating a particular communication link via which remote driving control of VNS 210 via network 250 can be implemented at system 260. In some embodiments, where the remote control request is generated at module 222, the request signal can include the authorization signal, so that the remote control system can determine that a remote control request signal received at system 262 includes an authorization of the remote driving control of the vehicle 200. System 264 can generate an authorization confirmation signal which indicates, to VNS 210, that system 260 has confirmed authorization of remote driving control of vehicle 200, based on determining that an authorization signal indicating authorization of remote driving control of vehicle 200 is received.

System 260 includes a navigation system 266 which is configured to generate remote driving command signals, also referred to herein as remote driving commands, which are communicated to VNS 210 over network 250 and, when received at VNS 210, are executed by the VNS 210 to navigate the vehicle 200 according to the remote driving command signals, so that vehicle is navigated according to remote driving control of vehicle 200 at system 260. VNS 210 includes a navigation control module 224 which receives and processes remote driving commands which are generated at system 266 and communicated to VNS 210 over network 250, and module 224 generates one or more sets of control element signals which cause one or more control elements 212 in the vehicle 200 to navigate the vehicle 200 according to the remote driving command signals.

In some embodiments, module 224 communicates sensor data generated by one or more sensors 216 to system 260 over network 250. System 260 includes a control interface 268 which can provide sensor data generated at one or more sensors 216, and communicated to system 260 via network 250, to one or more operators 270. In some embodiments, control interface 268 includes a display interface which provides one or more graphical representations of the vehicle 200 in an external environment, where the graphical representation is generated at system 260 based on the sensor data received from vehicle 200 over network 250. Interface 268 can include one or more sets of driving control interfaces via which an operator 270 can interact to generate one or more driving commands. System 266 can process the driving commands and, based on the processing, generate one or more sets of remote driving commands which are communicated to VNS 210 over network 250.

In some embodiments, the remote control system 260 can selectively engage in remote driving control of a vehicle based on communication with a separate user device 230 which supports a separate user 240.

In some embodiments, remote control system 260 authorizes remote driving control of a vehicle 200 based on interaction with a user device 230. In some embodiments, the remote control request signal generated at module 222 includes information identifying one or more user profiles, user devices, etc. associated with authorizing the request, and system 260 generates an authorization request signal, based on the information, which is transmitted to device 230 via network 250 and includes a request for authorization of remote driving control of vehicle 200. The authorization request signal can include vehicle identity information received from vehicle 200 in the remote control request signal which identifies the vehicle 200.

System 260 can determine whether to generate an authorization request signal to device 230 based on a determination, at system 262, regarding whether the request signal received from vehicle includes authorization of the remote driving control. Module 222 can determine whether to include authorization of the remote driving control in the request signal communicated to system 260 based on an identity of one or more users located in the vehicle 200. For example, where module 222 determines that an occupant of the vehicle 200 is not associated with a stored authorized user profile, module 222 can decline from including an authorization indication in the request signal. Where module 222 determines that an occupant of the vehicle 200 is associated with a stored authorized user profile, for example based on facial recognition monitoring of the occupant, interaction with a user device in proximity to the occupant, etc. module 222 can include an authorization indication in the request signal.

The authorization signal communicated from system 260 to device 230 can include an authorization request for a user 240 supported by the device 230 to authorize remote driving control of the vehicle 200. Device 230 includes an authorization module 236 which can process the authorization module received from system 260 and can provide to the user 240, via an interface 232 included in the device 230, an indication of the request for remote driving control authorization. Based on user interaction with the interface 232, module 236 can determine whether remote driving control of vehicle 200 is authorized. Where module 236 determines that remote driving control of vehicle 200 is authorized, module 236 can generate an authorization signal, which can include authorization information 238, which is communicated to system 260.

Authorization system 264 can process the message received from device 230 and can determine, based on processing the authorization information 238 included in the message received from device 230, that the user 240 supported by device 230 has authorized remote driving control of vehicle 200. In response, system 260 can engage remote driving control of vehicle 200, which can include commanding VNS 210 to communicate sensor data generated by one or more sensors 216, providing representations of the vehicle 200 in the environment to operator 270 via interface 268, and generating remote driving commands to VNS 210 based on operator 270 interaction with an interface 268, which causes the VNS 210 to navigate the vehicle according to the driving control command signals.

In some embodiments, a remote control request signal is generated at device 230, and communicated to system 260 over network 250, based on user 240 interaction with interface 232 of device 230. Device 230 includes a remote access module 234 which is configured to generate a remote control request signal based on user interaction with interface 232. The request signal generated at module 234 can include vehicle identity information which identifies vehicle 200, user identity information which identifies user 240, some combination thereof, etc.

In some embodiments, system 260 is configured to generate an authorization request signal to a particular VNS 210 of a particular vehicle 200 based on information included in a remote control request signal received from device 230. Where the signal received from device 230 includes user identity information identifying user 240, system 260 is configured to correlate the user identity information with vehicle identity information that identifies a vehicle which is associated with the user identity information. Vehicle identity information can include contact address information which specifies a contact address via which system 260 can communicate with vehicle 200 via network 250, a password via which a communication link with the vehicle 200 can be established, some combination thereof, etc.

Based on identifying vehicle 200 based on information included in a request signal received from device 230, system 260 can generate an authorization request signal which includes a request for VNS 210 to authorize remote driving control of vehicle 200 by system 260. The authorization request signal can include information identifying one or more of user 240, device 230, etc. Module 225 can respond to the authorization request signal by determining a match between the user identity information included in the authorization request signal with at least some user identity information included in stored set of authorized user profiles. Based on determining the match, module 225 can generate an authorization signal which indicates, to system 260, that remote driving control of vehicle 200 is authorized.

In some embodiments, remote driving control is engaged based on an audio communication link between a device supporting a user and the remote control system 260. Remote driving control, by system 260, of vehicle 200 can be engaged based at least in part upon an audio communication between one or more of a user 240 and an occupant of vehicle 200 and system 260. For example, an occupant of vehicle 200 can establish a communication link with system 260 via interaction with one or more user interfaces of vehicle 200 and can communicate, via the communication link, a request for emergency assistance to one or more of the system 260, an operator supported by the system 260, etc. Such a communication can include an emergency distress message, also referred to as a "911 call". In some embodiments, the system 260 is configured to determine that an occupant is requesting that remote driving control of vehicle 200 be engaged, based on processing the communication, and can generate an authorization request signal in response. In some embodiments, the communication is provided to an operator supported by system 260, and system 260 selectively generates an authorization request signal based on operator interaction with one or more interfaces 268 of the system 260 in response.

FIG. 3A-D illustrates interactions between the remote control system, a vehicle, and a user device associated with selectively engaging remote driving control of the vehicle at the remote control system, according to some embodiments.

FIG. 3A illustrates communication of a remote control request to remote control system 260 via a communication network 250, where the request is processed at a request processing system 262 of system 260 and system 262 determines, based on the processing, that remote driving control of vehicle 200 is requested.

In some embodiments, the remote control request is generated at an access request module 222 of vehicle 200 and is communicated from vehicle 200 to system 260 as signal 310 over network 250. Module 222 can generate the remote control request based on determining that one or more monitored conditions at least meets a threshold value. The determining can include a determination that a monitored health state parameter associated with at least one occupant of an interior of the vehicle 200, at least one individual external to the vehicle 200, some combination thereof, etc. at least meets one or more emergency health state parameter thresholds For example, where module 222 determines, based on processing sensor data generated by one or more sensor devices included in vehicle 200, that a monitored health state parameter of an occupant of the vehicle 200 at least meets an emergency health state threshold, module 222 can, in response, generate a remote control request signal 310 which is communicated to system 260 can comprises a request for system 260 to engage in remote driving control of vehicle 200.

In some embodiments, module 222 generates signal 310 based at least in part upon a remote driving control request signal 322 received from a user device 230 supporting one or more authorized users. In some embodiments, device 230 includes a remote access module 234 which is configured to generate a remote control request signal 322 which is transmitted to vehicle 200, and causes module 222 to generate remote control request signal 310, based on user interaction with one or more user interfaces of device 230. The signal 322 can include information identifying a user profile associated with the user supported by device 230, and module 222 can generate signal 310 based on determining a match between the user profile identified in the signal 322 with an authorized user profile stored at vehicle 200.

In some embodiments, a remote control request signal is generated at the user device 230 instead of vehicle 200 and is communicated from device 230 to remote control system 260 as signal 320 via communication network 250. In some embodiments, remote access module 234 is configured to generate a remote control request signal 320 which is transmitted to remote control system 260, based on user interaction with one or more user interfaces of device 230. The signal 320 can include information identifying one or more of a user profile associated with the user supported by device 230, a particular vehicle 200, etc.

FIG. 3B illustrates authorization of remote driving control of vehicle 200 at remote control system 260 via communication between the system 260 and one or more of vehicle 200 and user device 230 via network 250.

In some embodiments, remote control system 260 includes an authorization system 264 which, based on receipt of a remote control request signal 310, 320 from one or more of the vehicle 200 or the device 230 at system 260 as shown at FIG. 3A., generates an authorization request signal which requests one or more of a vehicle 200 or user device 230 to provide authorization of the remote driving control requested in the signal 310, 320.

In some embodiments, where the request signal received at the request processing system 262 of remote control system 260 includes a signal 320 communicated from module 234 of user device 230, the signal can include vehicle identity information which identifies a vehicle 200 for which remote driving control is requested and address information via which system 260 can communicate with vehicle 200 over network 250. System 264 can, based on the vehicle identity information included in the request signal 320, generate an authentication request signal 331 which is communicated to vehicle 200 and includes a request to authorization of remote driving control of the vehicle at system 260. The signal 331 can include user identity information included in the signal 320, and module 225 can compare the user identity information included in signal 331 which a stored set of authorized user identities. Module 225 can, based on determining a match between a user profile which is identified in the authorization request signal 331 and a stored set of authorized user profiles, generate an authorization signal 332, which can include information indicating authorization of remote driving control of vehicle 200, which is communicated to system 260 via network 250.

In some embodiments, where the request signal received at the request processing system 262 of remote control system 260 includes a signal 310 communicated from module 222 of vehicle 210, the signal can include user identity information which identifies a user who can authorize the requested remote driving control. In some embodiments, the user identity information includes contact address information which identifies a user device 230 which can be contacted to request authorization. In some embodiments, the user identity information includes information identifying a user profile associated with a user which can be contacted to request authorization, and system 264 can, based on the user identity information, identify a particular user device 230 associated with the user profile. Based on identifying a user device 230 associated with the user identity, system 264 can generate an authorization request signal which is communicated 333 to the user device 230 via network 250. The device 230 includes a module 236 which can provide a user supported by the device 230 with an indication of the authorization request signal and can, based on a user-initiated command to authorize the remote driving control of vehicle 200, generate an authorization signal which can include information indicating authorization of the remote driving control of vehicle 200 and is communicated 333 to system 260 via network 250.

In some embodiments, an authorization signal which indicates authorization of the remote driving control of vehicle 200 can include communication data which enables remote driving control of the vehicle 200. For example, the authorization signal can include a password which, when included with remote driving command signals communicated to the vehicle 200, causes a navigation control module 224 of the vehicle 200 to execute the remote driving commands based on determining that the password correlates with a stored password which is associated with the vehicle. The password can be stored at one or more of modules 225 in vehicle 200 and module 236 at device 230, and authorization signals generated at one or more of modules 225, 236 and indicating authorization of remote driving control of vehicle 200 can include the stored password associated with vehicle 200.

FIG. 3C illustrates vehicle 200 being navigated based on remote driving control of the vehicle 200 at remote control system 260 via a communication link 341 over network 250. System 260 includes a navigation control system 266 which is configured to, based on receiving authorization of remote driving control of vehicle 200, establish a two-way communication link 341 between the system 260 and the vehicle 200 via communication network 250. System 266 is configured to generate remote driving command signals which are communicated to the navigation control module 224 of vehicle 200 via link 341, where the navigation control module generates control element commands to various control elements of the vehicle 200 which cause the vehicle 200 to be navigated according to the remote driving commands generated at control system 266. Control system can generate a remote driving control initiation command which is communicated to vehicle 200 over link 341 and, when received at module 224, is executed by module 224 and causes the module 224 to establish the driving control mode of vehicle 200 as the remote driving control mode, which includes commanding the module 224 to selectively generate control element commands based on remote driving commands received from system 266 via link 241. The module 224 can selectively execute remote driving commands based on determining whether the remote driving commands include a password, key, etc. associated with the vehicle 200, where the module responds to identification of the password, key, etc. in a remote driving command by determining that the remote driving command is an authentic command. The module can compare a password, key, etc. included in a received remote driving command with a stored password, key, etc. and can determine authenticity of the remote driving command based on determining that the password, key, etc. in the remote driving command matches the stored password, key, etc.

Module 224 can, in response to receiving a remote driving control initiation command, generate sensor data signals which include sensor data generated by one or more sensor devices included in the environment and are communicated to system 260 via link 341. The control interface 268 included in system 260 can process the sensor data included in the sensor data signals and can generate a representation of the vehicle 200, the surrounding environment in which the vehicle is located, and one or more various parameters associated with the vehicle (e.g., velocity, acceleration, proximity to various elements in the environment, etc. which is provided to an operator via one or more interfaces. Control system 266 can generate remote driving commands based on operator interaction with one or more portions of the interface 268.

As shown in FIG. 3C, additional signals 342 can be communicated between remote control system 260 and device 230 via network 250, and additional signals 343 can be communicated between vehicle 200 and device 230. The signals 342, 343 can include signals indicating one or more parameters associated with the vehicle (e.g., velocity, acceleration, proximity to various elements in the environment, etc., an indication that the vehicle is in remote driving control mode, etc.

FIG. 3D illustrates remote control system 260 terminating remote driving control of vehicle 200. System 266 can determine to terminate remote driving control of vehicle 200 based at least in part upon one or more of a user-initiated command generated at interface 268, a determination, based on received sensor data from vehicle 200, that the vehicle 200 is located at a particular location proximate to one or more particular elements in the environment, etc. For example, system 266 can determine, based on processing sensor data received from vehicle 200 via network 250, that the vehicle is stopped within a threshold proximity of a particular static element in the environment, including a hospital. The system 266 can provide an operator with a prompt to command remote driving control termination, via interface 268. Based on determining that remote driving control is to be terminated, system 266 can generate a reset control signal which is communicated 351 to vehicle 200 via network 250. Module 224, upon receiving the reset control signal, can disable remote driving control mode of the vehicle 200, which can include switching the driving control mode of the vehicle to autonomous driving control and engaging in autonomously navigating the vehicle along a selected driving route to a selected location, including a proximate parking space.

In addition, based on determining that remote driving control is terminated, one or more of system 260 and vehicle 200 can generate reset control signals 352, 353 which can be communicated to device 230 and can include a message, which can be provided to a user via interface 232, indicating that remote driving control of vehicle 200 is terminated.

In some embodiments, system 266 can generate control systems which are communicates 351 to vehicle 200 via network 250 and, when received, are executed by one or more portions of the vehicle 200 to control one or more various devices included in the vehicle 200. For example, system 266 can generate remote control device commands which, when communicated to vehicle 200 via network 250, are executed by one or more portions of the vehicle to control one or more remote control devices according to the remote control device commands. Such remote control device commands can include commands to activate one or more remote control device light indicators, audio speakers, etc. In some embodiments, system 266 can generate commands which are executed by one or more portions of vehicle 200 to control door locks in one or more of the doors included in the vehicle.

In some embodiments, remote control system 260 is configured to remotely navigate vehicle 200, based on remote driving control of the vehicle 200, in response to a determination that the VNS 210 is unable to autonomously navigate the vehicle 200 under a particular set of conditions. Such a determination can be based on monitoring, at one or more of the system 260, VNS 210, etc. sensor data provided by one or more sensors 216 included in the vehicle 200, and the particular set of conditions can include the sensor data having at least a certain minimum level of quality. As a result, system 260 can navigate vehicle 200 via remote driving control in response to sensor 216 data degradation. In addition, the particular set of conditions can include a present of a human adult within one or more particular portions of the vehicle 200 interior. For example, a remote driving control request to system 260 can be generated by VNS 210 based on a determination, at VNS 210, that a human adult is absent from one or more particular portions of the vehicle interior, including one or more of a driver position, a front-seat position, some combination thereof, etc.

In some embodiments, system 260 is configured to navigate vehicle 200 to one or more particular positions, via remote driving control of vehicle 200 by system 260, to cause the vehicle to be positioned at a particular location. For example, where system 260 is associated with a valet parking service, the system 260 can receive a request, from one or more of the vehicle 200, a user device 230 supporting an authorized user 240, etc. for the vehicle 200 to be valet parked. In response, system 260 can engage remote driving control of vehicle 200 and navigate the vehicle 200 to a parking position. In response to receiving a request to navigate the vehicle to another position where an occupant can retrieve the vehicle, the system 260 can navigate the vehicle 200 to the other position and can hand off driving control to one or more of manual driving control, local autonomous driving control by the VNS 210, etc.

Figure 4:
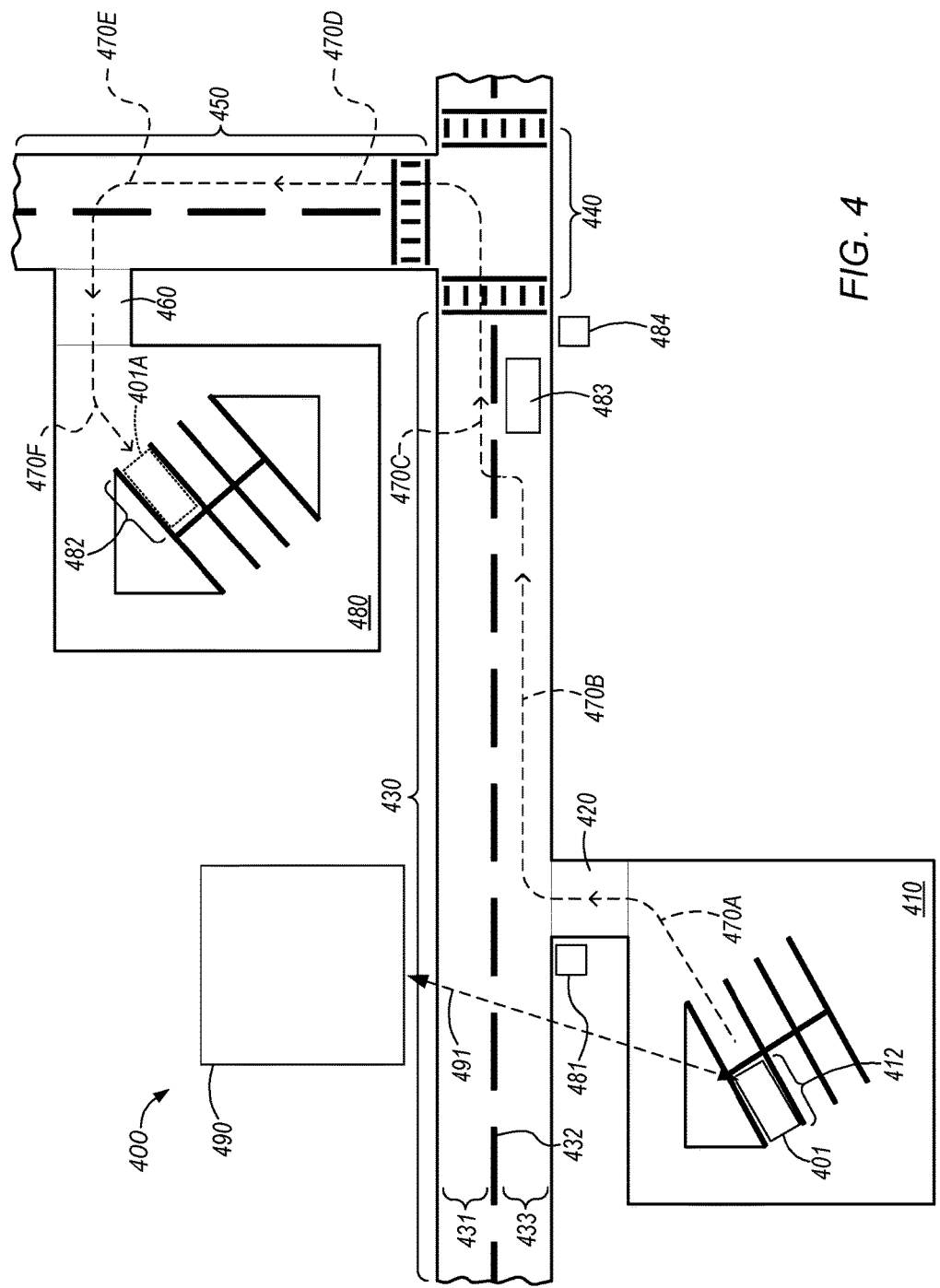
FIG. 4 illustrates an overhead view of a stopped vehicle which includes an impaired occupant being autonomously navigated from a starting position to a selected driving destination location, according to some embodiments.

FIG. 4 illustrates an overhead view of a stopped vehicle which includes an impaired occupant being autonomously navigated from a starting position to a selected driving destination location, according to some embodiments. The vehicle illustrated in FIG. 4 includes a VNS included in any of the embodiments herein.

In some embodiments, a VNS included in a vehicle 401 is configured to navigate the vehicle 401, based on control element signals generated by the VNS which causes various control elements included in the vehicle to control one or more aspects of the vehicle, etc., based on remote driving commands received at the VNS from a remotely-located remote control system 490 via a two-way communication link 491 between the vehicle 401 and the system 490. As a result, vehicle 401 is navigated through the environment 400 according to remote driving control of vehicle 401 at remote control system 490.

Remote driving control of vehicle 401 can be engaged based at least in part upon a determination, at a VNS included in the vehicle, that one or more health state parameters of an occupant of the vehicle at least meet one or more emergency state thresholds. When remote driving control of vehicle 401 at system 490 is engaged, a control system included in system 490 can generate remote driving commands, based on operator interaction with an interface included in the system 490, which causes the vehicle 401 to be navigated to a particular location in the environment.

As shown in FIG. 4, vehicle can be navigated, via remote driving control, to one or more of a selection of driving destinations. The selection can be provided to an operator at system 490, via one or more interfaces, and a particular selected destination 480 can be determined, and a driving route along which vehicle 401 can be navigated to destination 480, based on operator-initiated selection of the particular destination 480 from the selection of driving destinations.

FIG. 4 illustrates a geographic region 400 which includes a first driving location 410 at which a vehicle 401 is stopped in a particular location 412. As shown, the driving destination 410 is a parking lot which comprises a set of parking spots 412, and where the location 412 in which the stopped vehicle 401 is located is a particular parking spot.

Vehicle 401 includes a VNS which has engaged remote driving control of vehicle 401 at system 490, based at least in part upon a determination that at least one occupant of the vehicle interior is associated with one or more particular health states, including an emergency health state. The vehicle 401 is controlled by the VNS based on remote driving commands received from system 490 via link 491.

As shown in FIG. 4, when the vehicle 401 is stopped and remote driving control of the vehicle 401 is engaged, the vehicle 401 can be autonomously navigated to a second driving destination 480, and in particular to a driving destination location 482 associated with the driving destination 480, via a route 470A-E along various roadways 420, 430, 440, 450, 460. Such navigation can include the VNS navigating the vehicle 401 according to remote driving commands received via link 491 from location 412 to destination 480, where the VNS can refine the destination of the route 470 to be location 482 when the vehicle 401 is proximate to destination 480, so that the vehicle can be stopped at location 482 as stopped vehicle 401A.

In some embodiments, the VNS included in vehicle 401 can navigate vehicle 401 along one or more various portions of a driving route based on remote driving commands which specify general navigation actions. For example, in the illustrated embodiments, the VNS included in vehicle 401, when stopped at location 412, can receive a remote driving command which generally specifies that the vehicle is to be navigated out of location 410 and into lane 433 of roadway 430, and the VNS included in vehicle 401 can respond to the remote driving command by generating a set of control element signals which cause control elements of the vehicle to accelerate the vehicle along a set of pathways 470A-B which result in the vehicle 401 being navigated through roadway 420 and into lane 433 of roadway 430. Similarly, VNS can generate sets of control element signals which cause vehicle 401 to be navigated along various portions 470C-F of the driving route according to general remote driving commands received from system 490.

In some embodiments, vehicle 401 can interact with various elements of the environment based on remote driving control of the vehicle being engaged. A vehicle 401 can include a set of remote control devices which are selectively activated or disabled based on whether the remote driving control of the vehicle is engaged or disabled, respectively. Where remote driving control of the vehicle is engaged, one or more of the remote control devices can interact with one or more elements of the environment to facilitate navigation of the vehicle through the environment. For example, where environment 400 includes elements 481, 484 which are traffic control signals which indicate whether traffic moving along one or more of roadways 420, 430 should move into subsequent roadways 430, 440, respectively, vehicle 401 can include a remote control device which can interact with one or more of the elements 481, 484 and can cause the elements to switch the provided indication so that the elements indicate that traffic in the lane in which the vehicle 401 is located can proceed to move. As a result, navigation of the vehicle 401 through environment 400 can be accelerated while maintaining proper regulation of traffic through the environment.

In some embodiments, where remote driving control of vehicle 401 is engaged, the vehicle 401 can be navigated in a manner which violates one or more various rules of the road. For example, where remote driving control is engaged, a VNS included in vehicle 401 can generate control element signals, based on remote driving commands received from system 490, which cause the vehicle 401 to be navigated at a velocity which exceeds a speed limit of the roadway on which the vehicle 401 is located. In another example, where vehicle 401 is being navigated along route 470B in lane 433 of roadway 430, and the vehicle 401 is approaching a stopped vehicle 483 at intersection 440, the VNS included in vehicle 401 can, based on received remote driving commands which command that vehicle 401 be navigated through intersection 440 and into roadway 450, navigate the vehicle 401 along a route 470C which navigates vehicle 401 into opposing-travel roadway lane 431 and into intersection 400 and a lane of roadway 450, even though navigating into lane 431 can result in violations of traffic laws. Such violations can be temporarily authorized as a result of the vehicle 401 being in a remote driving control mode. In some embodiments, VNS selectively generates control element signals which cause the vehicle 401 to be navigated in violation of a traffic law based on receipt of a remote driving command, from system 490, which includes an authorization to violate the traffic law. The authorization can include a specific authorization to violate a specific traffic law, a blanket authorization to violate a set of one or more various traffic laws, etc. The authorization can be restricted to navigation through a particular portion of the environment and can be retracted based on retraction signals received from system 490.

Figure 5:
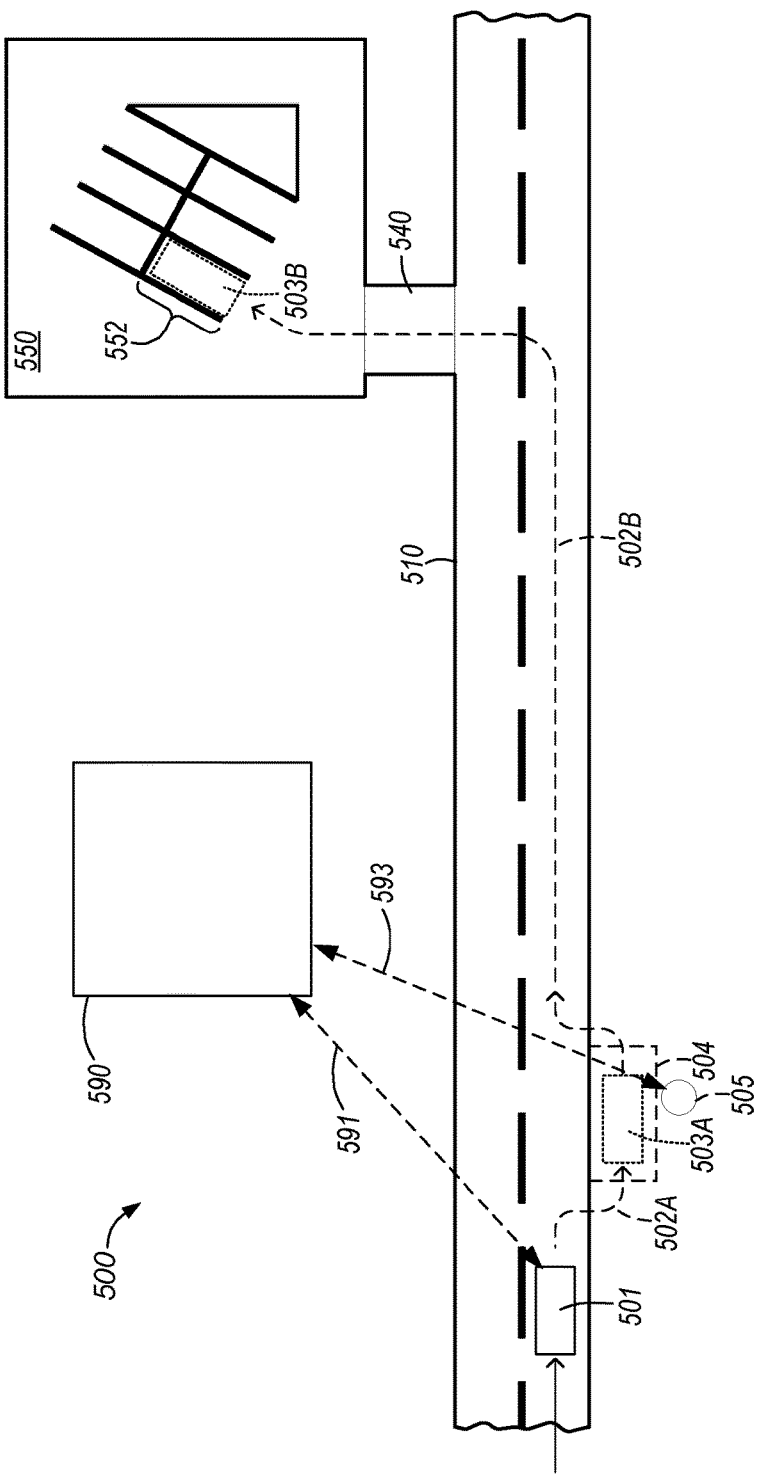
FIG. 5 illustrates an overhead view of a vehicle in motion which stops at a particular roadside location to pick up an individual at the roadside and then navigate the vehicle to a destination location via remote driving control, according to some embodiments.

FIG. 5 illustrates an overhead view of a vehicle in motion which stops at a particular roadside location to pick up an individual at the roadside and then navigate the vehicle to a destination location via remote driving control, according to some embodiments. The vehicle illustrated in FIG. 5 includes a VNS included in any of the embodiments herein.

In some embodiments, a vehicle can be navigated according to remote driving commands so that the vehicle is navigated to a stop proximate to a particular individual in the environment, whereupon the individual can enter the vehicle interior and the vehicle can be further navigated, via remote driving control, to a particular driving destination.

The individual can include an individual for whom a health emergency is determined by one or more vehicles, remote control systems, etc. In some embodiments, the individual interacts with a user device to generate a remote control request signal which is communicated 593 to remote control system 590. In response, the system 590 can communicate 591 a remote control authorization request to vehicle 501. The system 590 can selectively communicate with the particular vehicle 501 based on information included in the request signal communicated 593 from individual 505 which identifies the vehicle 501, a determination that vehicle 501 is within a certain proximity distance to individual 505, some combination thereof, etc.

The request signal communicated 593 from individual 505 to system 590 can include information indicating a roadside position 504 which is proximate to the individual 505. System 590 can utilize the position information to command vehicle 501 to be navigated 502A to a stop at position 504 as vehicle 503A. System 590 can control one o more portions of the vehicle 501, including door actuators, door locks, etc. Based on determining, based on one or more internal sensors, external sensors, etc. that the individual 505 enters the vehicle 501, system 590 can generate remote driving commands which are communicated to vehicle 501 via link 591 can cause the vehicle 501 to be navigated 502B from position 504, along roadways 510, 540, to a destination 550 selected at system 590. In some embodiments, a VNS included in vehicle 501 can respond to a remote driving command from system 590 to navigate the vehicle 501 designation 550 by selecting a particular location 552 associated with the destination 550 and navigating the vehicle 501 to a stop at the location 552 as vehicle 503B.

In some embodiments, vehicle 501 can utilize one or more remote control devices to communicate information to individual 505 when vehicle 501 is stopped at position 504 as vehicle 503A. Such communication can include generating a predetermined audio message to the individual, including a command to the individual 505 to enter the vehicle interior, communicating an audio message generated at system 590 based on operator interaction with an audio interface, etc. In some embodiments, the vehicle 501 includes a remote control device which enables two-way audio communication between an operator at remote control system 590 and individual 505.

Figure 6:
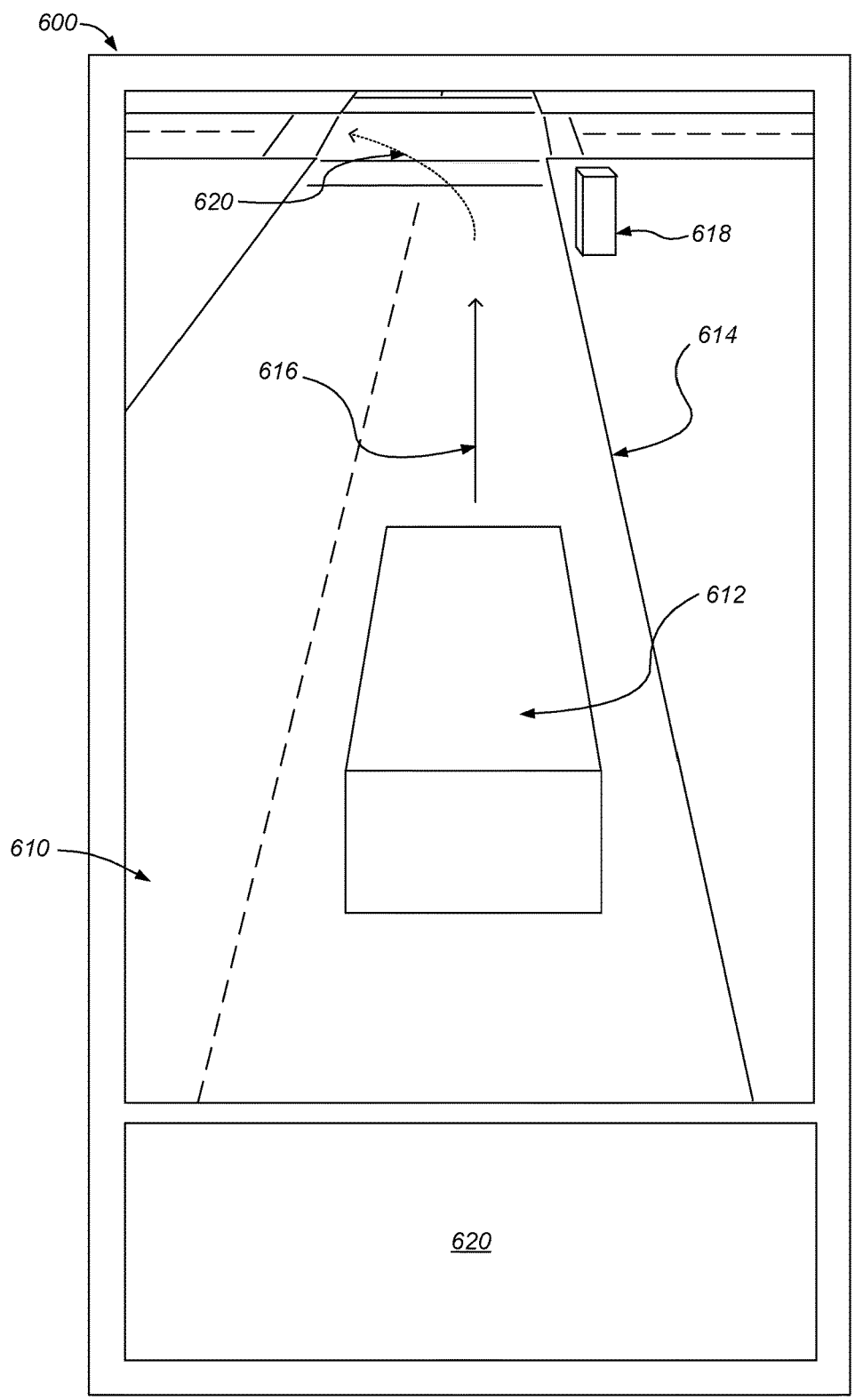
FIG. 6 illustrates a control interface of a remote control system, according to some embodiments.

FIG. 6 illustrates a control interface of a remote control system, according to some embodiments. The control interface illustrated in FIG. 6 can be included in any of the embodiments of remote control systems included herein.

In some embodiments, a control interface included in a remote control system includes a graphical display via which an operator interacting with the interface to remotely control navigation of a vehicle through an environment can view a graphical representation of the vehicle in the environment. The control interface can include one or more sets of driving control interfaces via which the operator can interact to control navigation of the vehicle through the environment. The graphical representation can be generated based on sensor data generated at one or more sensor devices included in the vehicle and communicated to the remote control system.

FIG. 6 illustrates a control interface 600 which includes a graphical display 610 and a set of driving control interfaces 620. As shown, the graphical display 610 includes a graphical representation of a vehicle 612 in an external environment, where the environment includes a roadway network 614 on which the vehicle is located, one or more static elements 618 located in the environment, etc.

The graphical representation illustrates a third-person view, also referred to as overhead view, bird-eye view, etc. of the vehicle 612 and can be generated based on sensor data generated by one or more sensor devices included in the vehicle 612 and communicated to a remote control system in which the interface 600 is located. An operator can interact with interface 620 to cause vehicle 612 to be navigated through the environment.

The graphical representation includes a representation 616 of the present navigation of the vehicle 612 through the external environment. The representation 616 provides an indication of the present direction and velocity of the vehicle 612 along roadway 614 and can be generated based at least in part upon one or more of operator interactions with interface 620, sensor data received at a remote control system from vehicle 612, etc.

The graphical representation includes a representation of navigation cues 620 along which vehicle 612 can be navigated, based on operator interaction with interface 620, to navigate vehicle 612 to a particular selected driving destination. The driving destination can be selected based on operator interaction with interface 620 to select a particular driving destination from a selection of driving destinations, and interface 600 can generate a set of navigation cues which indicate a driving route along which the vehicle 612 can be navigated through the environment to be navigated to the particular driving destination.

Figure 7:
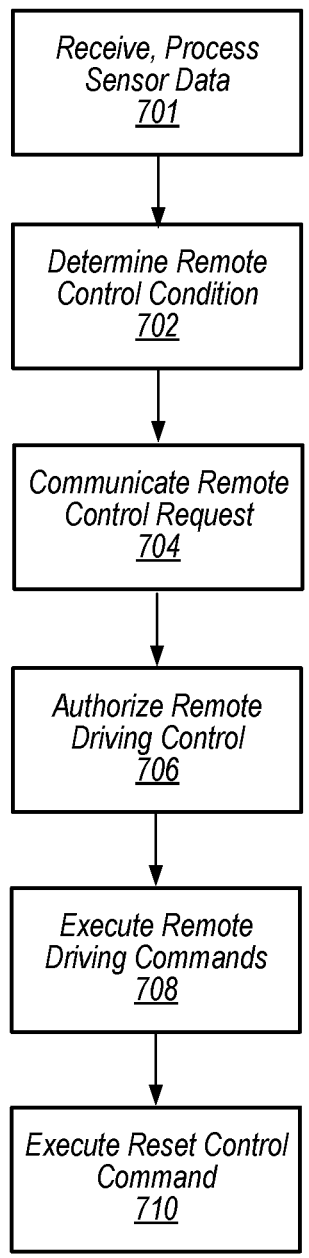
FIG. 7 illustrates executing remote driving control at a vehicle navigation system (VNS) included in a vehicle, according to some embodiments.

FIG. 7 illustrates executing remote driving control at a vehicle navigation system (VNS) included in a vehicle, according to some embodiments. The vehicle navigation system can include any of the embodiments of a vehicle navigation system included herein and can be implemented by one or more computer systems.

At 701, one or more instances of sensor data, generated by one or more sensor devices included in a vehicle, are received and processed at the VNS. Sensor data can be received from multiple different sensor devices. Sensor data can include images captured by one or more camera devices, chemical substance data indicating a presence and concentration of chemical substances in the vehicle interior, some combination thereof, etc.

Sensor data processing can include determining a value for one or more health state parameters associated with an occupant of one more particular positions of the vehicle interior, an individual located external to the vehicle within a certain threshold proximity, some combination thereof, etc.

At 702, a remote control condition is determined at the VNS. A remote control condition can include a determination that remote driving control of the vehicle is to be established and executed, and the determination can be made based on a determination of a health emergency with regard to one or more vehicle occupants, external individuals, etc. for which health state parameters of the occupant, individual, etc. are determined at 702.

In some embodiments, processing sensor data can include comparing a determined value for one or more health state parameters associated with an occupant of the vehicle interior with one or more emergency health state threshold values for the one more health state parameters. Health state parameters can include one or more of occupant eye pupil dilation, occupant blinking rate, occupant heart rate, occupant head motion frequency, atmospheric concentration of one or more chemical substances in the vehicle interior, quantity and magnitude of manually-induced navigation errors, some combination thereof, etc.

A determination that an occupant, individual, etc. is associated with an emergency health state can include a determination that whether one or more determined parameter values associated with one or more occupants, individuals, etc. exceeds an emergency heath state threshold associated with the parameter values. For example, where a parameter value for an occupant in the driver position is determined, via processing of sensor data at 701, to be a heart rate (also referred to as "heartbeat rate", etc.), a determination of whether the health state parameter value exceeds an emergency health state threshold can include determining whether the determined occupant heart rate exceeds a threshold level of heart rate. In some embodiments, an emergency health state threshold is associated with a health state at which an occupant having such a health state is impaired from being able to manually navigate the vehicle to at least a particular predetermined level of precision.

The threshold level can be specific to the particular identified occupant for which the health state parameter values are determined. Determining whether an emergency health state threshold value is exceeded can include tracking one or more health state parameter values of an occupant over time and determining if the one or more health state parameter values exceed the emergency health state threshold value associated with the one or more health state parameter values for at least a threshold amount of elapsed time.

If one or more parameter values associated with an occupant located in one or more particular positions in the vehicle interior are determined to exceed a health emergency threshold value, a determination can be made that the occupant is associated with a health emergency. A determination of a remote control condition at 702 can be based on the determination that the occupant is associated with the health emergency.

In some embodiments, a remote control condition is determined based at least in part upon manual interaction with one or more user interfaces included in the vehicle. For example, where a user interface included in the vehicle includes an interactive element associated with engaging remote control of the vehicle, the VNS can determine a remote control condition based upon interaction, by one or more occupants of the vehicle, with the interactive element included in the user interface.

At 704, a remote control request is generated at the VNS and communicated to a remote control system which is external to the vehicle in which the VNS is located. The request can include a request for the remote control system to engage remote driving control of the vehicle, a request to navigate the vehicle to one or more particular locations, sensor data generated by one or more sensor devices of the vehicle, health state parameter data determined based on the processing at 701, vehicle identity data identifying the vehicle for which remote driving control is requested, some combination thereof, etc.

At 706, remote driving control of the vehicle is authorized at the VNS. Such authorization can include generating an authorization signal which can include a message which indicates authorization of the remote control system to engage remote driving control of the vehicle, a password which can be used by the remote control system to communicate authorized remote driving commands which will be accepted and executed by the VNS included in the vehicle, some combination thereof, etc. The authorization signal can be generated based on receipt of an authorization request signal from the remote control system. The authorization request signal can include one or more instances of identity data, including vehicle identity data, user identity data, etc., and the authorization signal can be generated based on one or more of a determination that the vehicle identity data included in the authorization request signal matches vehicle identity data associated with the vehicle in which the VNS is located, a determination that the user identity data included in the authorization request signal matches at least one user profile associated with an authorized user, some combination thereof, etc. In some embodiments, the authorization signal is generated based on the remote control request being generated at 704 and independently of any authorization request signal from the remote control system.

At 708, remote driving commands received at the VNS from the remote control system are executed at the VNS, which results in the vehicle in which the VNS is included being navigated through an environment based on remote driving control of the vehicle at the remote control system. Received remote driving commands can be executed based on a determination, at the VNS, that the received remote driving commands are authorized commands. A determination that a received remote driving command is an authorized command can include a determination that the received remote driving command includes a password which matches a locally-stored password associated with authorized remote driving commands. The VNS can selectively execute a received remote driving command based on whether the received remote driving command includes the matching password.

Executing a received remote driving command can include processing the remote driving command, determine a driving action commanded by the remote driving command, generating a set of control element commands based on the commanded driving action, and transmitting the set of control element commands to a set of control elements included in the vehicle. The control elements, upon executing the set of control element commands, cause the vehicle to be navigated according to the commanded driving action.

Executing a remote driving command at 708 can include switching the driving control mode of the VNS to a remote driving control mode, which results in the VNS selectively executing remote driving commands and inhibiting manual driving control of the vehicle via one or more interfaces included in the vehicle. In some embodiments, the VNS is configured to switch from remote driving control to local autonomous driving control, local manual driving control, etc., based on interaction by an occupant of the vehicle with one or more user interfaces included in the vehicle. For example, the VNS can execute the reset command 710 based on receiving an occupant-initiated command to disable remote driving control. In some embodiments, in response to receipt of a re-set command, the VNS can autonomously navigate the vehicle to a stopped position in a particular selected proximate location, including a roadway shoulder region, a proximate parking space, etc., whereupon manual driving control of the vehicle can be activated.

In some embodiments, the VNS communicates one or more instances of sensor data, generated by one or more sensor devices in the vehicle, to the remote control system based on authorizing remote driving control. As a result, the remote control system can use the sensor data to provide an operator which a representation of the vehicle in which the VNS is located in the environment, and the operator can utilize the representation to initiate commands upon which remote control system-generated remote driving commands are based. In some embodiments, the VNS generates one or more control commands to cause the vehicle to be navigated along a driving route which differs from the driving route along which the vehicle is being remotely navigated. For example, where the vehicle is being remotely navigated along a roadway, and the VNS determines that the present driving route of the vehicle is approaching within a threshold proximity to a static object in the roadway, the VNS can cause the vehicle to be navigated along a driving route which avoids intersection with the static element, thereby temporarily overriding remote driving control of the vehicle, and resuming remote driving control upon completion of the avoidance navigation. The VNS can estimate a driving route along which the vehicle is being remotely navigated, determine an avoidance driving route which departs from the estimated riving route and returns to the estimated driving route upon avoiding intersection with an element in the environment, execute the avoidance driving route, and resuming remote driving control of the vehicle upon returning the vehicle to the estimated driving route. The VNS can transmit a signal to the remote control system which provides indication that the VNS is navigating the vehicle along an avoidance driving route upon determining and executing the avoidance driving route.

At 710, the VNS executes a reset control command to terminate remote driving control mode of the VNS, based on receipt of a reset control command from the remote control system. The VNS, in executing the reset control command, can switch from remote driving control mode to autonomous driving control mode and can autonomously navigate the vehicle to a standby location, including a determined proximate available parking space. Executing the reset control command can include terminating sensor data communication to the remote control system, terminating one or more communication links with the remote control system, etc.

In some embodiments, the VNS communicates with a user device supporting a particular user based on executing remote driving control. For example, in some embodiments, the VNS can, based on executing any one or more of 701-710, generate a message which is communicated to the user device and indicates that the any one or more of 701-710 is being executed at the VNS, has been executed at the VNS, some combination thereof, etc.

Figure 8:
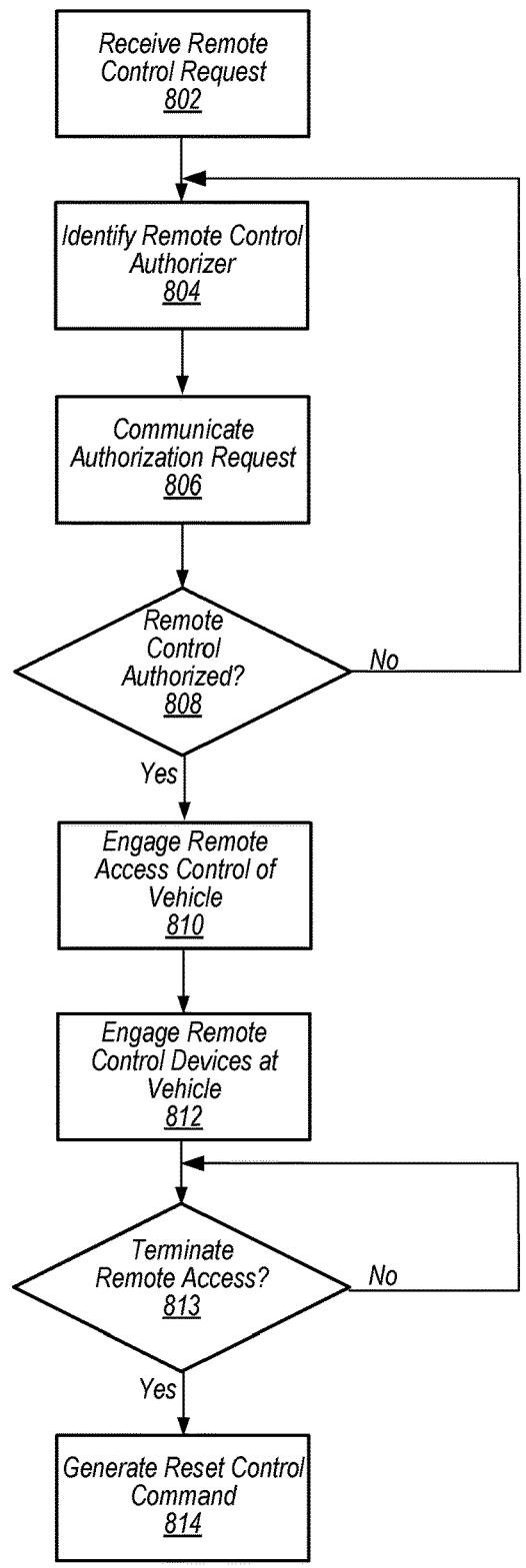
FIG. 8 illustrates executing remote driving control of a VNS included in a vehicle at a remote control system which is external to the vehicle, according to some embodiments.

FIG. 8 illustrates executing remote driving control of a VNS included in a vehicle at a remote control system which is external to the vehicle, according to some embodiments. The vehicle navigation system can include any of the embodiments of a vehicle navigation system included herein and can be implemented by one or more computer systems.

At 802, a remote control request is received at the remote control system. The remote control request includes a request to engage remote driving control of a vehicle, via remote driving control of the VNS included in the vehicle. The request can include vehicle identity data which identifies the vehicle for which remote driving control is requested.

In some embodiments, the remote control request is received from the vehicle for which remote driving control is requested. In some embodiments, the remote control request is received from a user device which is separate from the vehicle for which remote driving control is requested. In some embodiments, the remote control request includes one or more instances of user identity data which identify a particular user profile associated with the remote control request. For example, where the remote control request is received from a user device, the request can include, in addition to vehicle identity data indicating the vehicle for which remote driving control is requested, an instance of user identity data identifying the user who commanded the request.

At 804, an authorizer of remote driving control of the vehicle for which remote control is requested, referred to herein interchangeably as the remote control vehicle, is identified based on the remote control request. In some embodiments, the authorizer is the remote driving control vehicle itself. For example, where the remote control request is received from a separate user device, the remote control request can include vehicle identity data which identifies the vehicle, the VNS included in the vehicle, some combination thereof, etc. The identity data can include contact address data via which a communication link can be established between the remote control system and the vehicle, a password which can be utilized at the remote control system to establish the communication link, etc. The remote control system can determine, based on a determination that the remote control request is received from a user device which is separate from the remote control vehicle, that the remote control vehicle itself is the authorizer.

In some embodiments, the remote control system can access a database of authorizers associated with particular vehicles and can determine that one or more of the remote control vehicle, one or more user profiles associated with the remote control vehicle in the database, one or more user devices associated with the remote control vehicle in the database, some combination thereof, etc. are authorizers. In some embodiments, the remote control system can identify multiple authorizers of remote driving control of the vehicle, where a limited selection of the authorizers are required to authorize remote driving control of the remote control vehicle.

At 806, an authorization request to the authorizer is generated. In some embodiments, the authorization request includes a request for the authorizer to authorize remote driving control of the remote control vehicle. Where the authorizer is a user supported by a particular user device, a user associated with a particular user profile, user account, etc., the authorization request can include information identifying the remote control vehicle. Where the authorizer is the remote control vehicle itself, the authorization request can include information identifying a user profile, user device, etc. associated with the remote control request.

At 808 and 810, if remote driving control of the vehicle is authorized, remote driving control of the vehicle is engaged at the remote control system. A determination that remote driving control is authorized can include a determination that an authorization signal is received from at least one authorizer of remote driving control of the vehicle. The authorization signal can include password information associated with communicated authorized remote driving commands which will be selectively executed by the VNS included in the vehicle, and the remote control system can respond to identification of the password information included in the authorization signal by at least partially incorporating the password information into generated remote driving commands.

Engaging remote driving control of the vehicle at 810 includes providing an operator of the remote control system, via a control interface, with a graphical representation of the remote control vehicle in the environment in which it is located. The providing is based on sensor data received from the remote control vehicle. The sensor data can be generated at the remote control vehicle, and the sensor data can be processed at the remote control system to generate the graphical representation.

Engaging remote driving control of the vehicle at 810 includes generating remote driving commands which, when executed at the VNS included in the vehicle, cause the vehicle to be navigated according to the remote driving commands. Remote driving commands can be generated based on operator interaction with one or more control interfaces included in the remote control system. The operator can interact with the control interface based on the graphical representation of the vehicle in the environment provided to the operator.

At 812, one or more sets of remote control devices included in the remote control vehicle are engaged via device commands generated at the remote control system. The remote control devices can include one or more devices which are configured to provide externally-observable indications that the vehicle is being navigated via remote driving control, that the vehicle is being navigated based on a health emergency, etc. The remote control devices can include on or more devices which are configured to interact with one or more portions of the external environment, including one or more traffic control signals, to cause the one or more portions of the external environment to execute an operation which results in expediting navigation along a portion of the route along which the vehicle is being navigated via remote driving control. For example, a remote control device can include an infrared indicator which is configured to interact with an infrared sensor installed in a traffic control signal, so that the infrared indicator commands the traffic control signal to indicate that traffic navigating along the same roadway lane as the remote control vehicle is authorized to move along the lane, through an intersection, etc.

In some embodiments, one or more device commands comprises a command, to one or more portions of the remote control vehicle, to activate the remote control device. The command can include an authorization passcode which, when processed by the remote control device, causes the remote control device to selectively respond to the command. The remote control device can be configured to deactivate in the absence of receiving a command which includes the authorization passcode within a certain period of elapsed time.

In some embodiments, the device commands are communicated concurrently with the remote driving commands generated at the remote control system.

At 813 and 814, a reset control command is generated, which, when executed by the VNS in the remote control vehicle, causes remote driving control of the vehicle to be disabled, based on a determination that remote control is to be terminated. The determination can be based on a particular interaction of an operator which a control interface of the remote control system, including an operator-initiated command to terminate remote driving control of the vehicle. The determination can be based on a determination that the vehicle is in a particular location in the environment and is at a complete stop in the environment, based on processing one or more instances of sensor data received from the vehicle.

Figure 9:
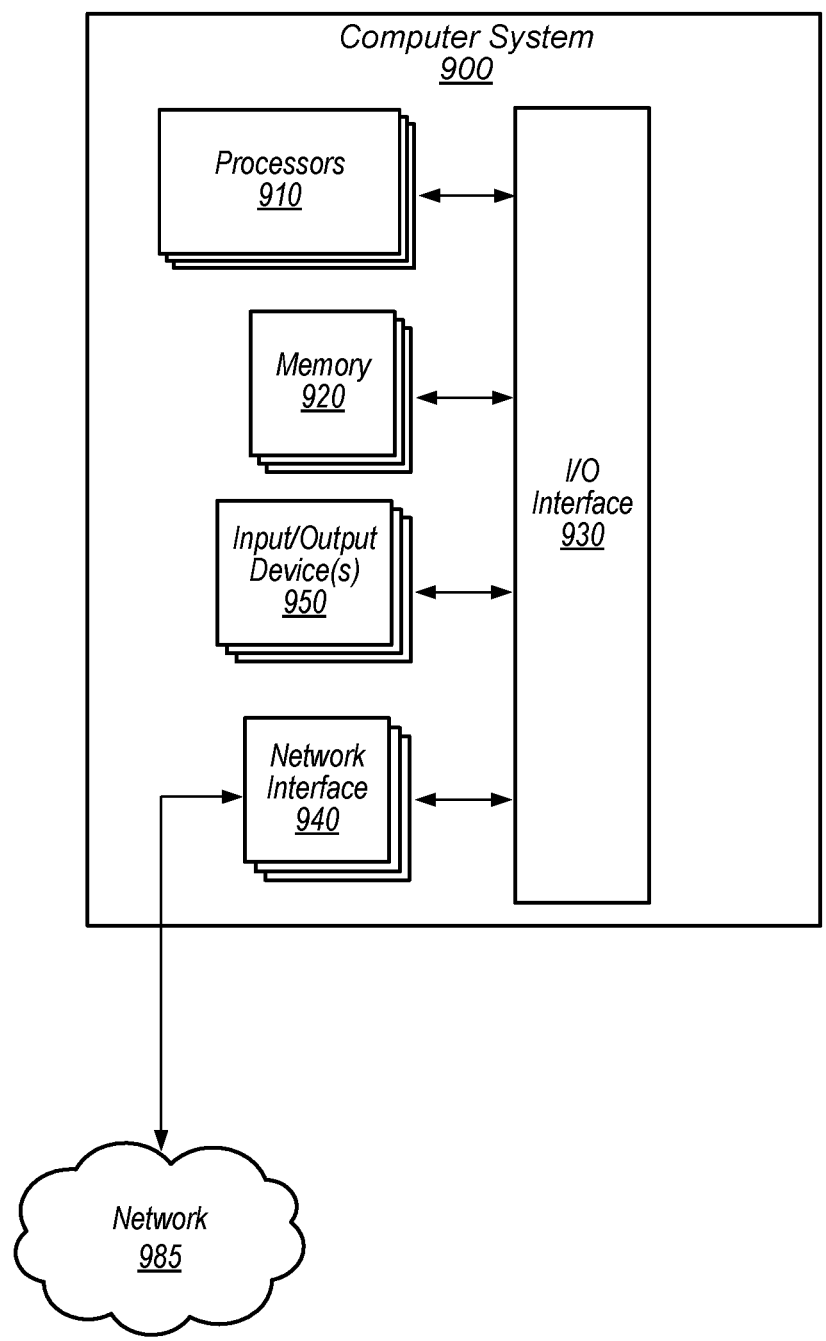
FIG. 9 illustrates an example computer system configured to implement aspects of a system and method for autonomous navigation, according to some embodiments.

FIG. 9 illustrates an example computer system 900 that may be configured to include or execute any or all of the embodiments described above. In different embodiments, computer system 900 may be any of various types of devices, including, but not limited to, a personal computer system, desktop computer, laptop, notebook, tablet, slate, pad, or netbook computer, cell phone, smartphone, PDA, portable media device, mainframe computer system, handheld computer, workstation, network computer, a camera or video camera, a set top box, a mobile device, a consumer device, video game console, handheld video game device, application server, storage device, a television, a video recording device, a peripheral device such as a switch, modem, router, or in general any type of computing or electronic device.

Various embodiments of a vehicle navigation system (VNS), a remotely-controlled vehicle navigation system, a remote navigation control system, etc. as described herein, may be executed in one or more computer systems 900, which may interact with various other devices. Note that any component, action, or functionality described above with respect to FIG. 1 through 8 may be implemented on one or more computers configured as computer system 900 of FIG. 9, according to various embodiments. In the illustrated embodiment, computer system 900 includes one or more processors 910 coupled to a system memory 920 via an input/output (I/O) interface 930. Computer system 900 further includes a network interface 940 coupled to I/O interface 930, and one or more input/output devices, which can include one or more user interface devices. In some cases, it is contemplated that embodiments may be implemented using a single instance of computer system 900, while in other embodiments multiple such systems, or multiple nodes making up computer system 900, may be configured to host different portions or instances of embodiments. For example, in one embodiment some elements may be implemented via one or more nodes of computer system 900 that are distinct from those nodes implementing other elements.

In various embodiments, computer system 900 may be a uniprocessor system including one processor 910, or a multiprocessor system including several processors 910 (e.g., two, four, eight, or another suitable number). Processors 910 may be any suitable processor capable of executing instructions. For example, in various embodiments processors 910 may be general-purpose or embedded processors implementing any of a variety of instruction set architectures (ISAs), such as the x86, PowerPC, SPARC, or MIPS ISAs, or any other suitable ISA. In multiprocessor systems, each of processors 910 may commonly, but not necessarily, implement the same ISA.

System memory 920 may be configured to store program instructions, data, etc. accessible by processor 910. In various embodiments, system memory 920 may be implemented using any suitable memory technology, such as static random access memory (SRAM), synchronous dynamic RAM (SDRAM), nonvolatile/Flash-type memory, or any other type of memory. In the illustrated embodiment, program instructions included in memory 920 may be configured to implement some or all of an automotive climate control system incorporating any of the functionality described above. Additionally, existing automotive component control data of memory 920 may include any of the information or data structures described above. In some embodiments, program instructions and/or data may be received, sent or stored upon different types of computer-accessible media or on similar media separate from system memory 920 or computer system 900. While computer system 900 is described as implementing the functionality of functional blocks of previous Figures, any of the functionality described herein may be implemented via such a computer system.

In one embodiment, I/O interface 930 may be configured to coordinate I/O traffic between processor 910, system memory 920, and any peripheral devices in the device, including network interface 940 or other peripheral interfaces, such as input/output devices 950. In some embodiments, I/O interface 930 may perform any necessary protocol, timing or other data transformations to convert data signals from one component (e.g., system memory 920) into a format suitable for use by another component (e.g., processor 910). In some embodiments, I/O interface 930 may include support for devices attached through various types of peripheral buses, such as a variant of the Peripheral Component Interconnect (PCI) bus standard or the Universal Serial Bus (USB) standard, for example. In some embodiments, the function of I/O interface 930 may be split into two or more separate components, such as a north bridge and a south bridge, for example. Also, in some embodiments some or all of the functionality of I/O interface 930, such as an interface to system memory 920, may be incorporated directly into processor 910.

Network interface 940 may be configured to allow data to be exchanged between computer system 900 and other devices attached to a network 985 (e.g., carrier or agent devices) or between nodes of computer system 900. Network 985 may in various embodiments include one or more networks including but not limited to Local Area Networks (LANs) (e.g., an Ethernet or corporate network), Wide Area Networks (WANs) (e.g., the Internet), wireless data networks, some other electronic data network, or some combination thereof. In various embodiments, network interface 940 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices may, in some embodiments, include one or more display terminals, keyboards, keypads, touchpads, scanning devices, voice or optical recognition devices, or any other devices suitable for entering or accessing data by one or more computer systems 900. Multiple input/output devices may be present in computer system 900 or may be distributed on various nodes of computer system 900. In some embodiments, similar input/output devices may be separate from computer system 900 and may interact with one or more nodes of computer system 900 through a wired or wireless connection, such as over network interface 940.

Memory 920 may include program instructions, which may be processor-executable to implement any element or action described above. In one embodiment, the program instructions may implement the methods described above. In other embodiments, different elements and data may be included. Note that data may include any data or information described above.

Those skilled in the art will appreciate that computer system 900 is merely illustrative and is not intended to limit the scope of embodiments. In particular, the computer system and devices may include any combination of hardware or software that can perform the indicated functions, including computers, network devices, Internet appliances, PDAs, wireless phones, pagers, etc. Computer system 900 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 900 may be transmitted to computer system 900 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium. Generally speaking, a computer-accessible medium may include a non-transitory, computer-readable storage medium or memory medium such as magnetic or optical media, e.g., disk or DVD/CD-ROM, volatile or non-volatile media such as RAM (e.g. SDRAM, DDR, RDRAM, SRAM, etc.), ROM, etc. In some embodiments, a computer-accessible medium may include transmission media or signals such as electrical, electromagnetic, or digital signals, conveyed via a communication medium such as network and/or a wireless link.

The methods described herein may be implemented in software, hardware, or a combination thereof, in different embodiments. In addition, the order of the blocks of the methods may be changed, and various elements may be added, reordered, combined, omitted, modified, etc. Various modifications and changes may be made as would be obvious to a person skilled in the art having the benefit of this disclosure. The various embodiments described herein are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

What is claimed is:

1. An apparatus, comprising:
  a vehicle navigation system configured to be installed in a vehicle and control one or more sets of vehicle control elements installed in the vehicle to cause the vehicle to be navigated through an environment in which the vehicle is located based on remote driving commands received from a remote control system, wherein the vehicle navigation system is configured to:
    transmit a remote control request signal, to the remote control system, based at least in part upon a determination that an occupant of an interior of the vehicle is associated with a health state which meets at least one threshold;

receive a remote control authorization request message from the remote control system; and authorize the remote control system for remote driving control of the vehicle, based at least in part on a determination that the remote control authorization request message includes authentication data for the vehicle.

2. The apparatus of claim 1, wherein the vehicle navigation system is configured to:

based at least in part authorization of the remote control system for remote driving control, transmit an authorization signal to the remote control system.

3. The apparatus of claim 1, wherein, to authorize remote driving control of the vehicle, the vehicle navigation system is configured to:

identify an instance of identity data included in the remote control authorization request message; and determine that the instance of identity data matches a locally stored instance of identity data.

4. The apparatus of claim 3, wherein:

the instance of identity data comprises an instance of identity data associated with a particular end user; and the locally stored instance of identity data comprises an instance of identity data associated with an authorized end user who is authorized to request remote driving control of the vehicle.

5. The apparatus of claim 3, wherein, to authorize remote driving control of the vehicle, the vehicle navigation system is configured to:

transmit an authorization signal which specifies password information via which the remote control system can engage remote driving control of the vehicle; and execute one or more remote driving command signals received from the remote control system, based at least in part on a determination that the one or more remote driving command signals include the specified password information.

6. The apparatus of claim 1, wherein the vehicle navigation system is configured to:

transmit a remote control request signal, to the remote control system, based at least in part upon user interaction with one or more user interfaces installed in the vehicle.

7. The apparatus of claim 1, wherein the vehicle navigation system is configured to:

authorize remote driving control of the vehicle concurrently with generating the remote control request signal, based at least in part upon the based at least in part upon user interaction with one or more user interfaces installed in the vehicle.

8. The apparatus of claim 1, wherein the vehicle navigation system is configured to:

selectively engage one or more sets of remote control devices based on one or more devices commands received from the remote control system, wherein the one or more sets of remote control devices are configured to provide externally-observable indications that the vehicle is being navigated via remote driving control.

9. A system, comprising:

a vehicle comprising one or more sets of vehicle control elements configured to cause the vehicle to be navigated through an environment in which the vehicle is located based on remote driving commands received from a remote control system; and a vehicle navigation system is configured to:

transmit a remote control request signal, to the remote control system, based at least in part upon a determination that an occupant of an interior of the vehicle is associated with a health state which meets at least one threshold;

receive a remote control authorization request message from the remote control system; and authorize the remote control system for remote driving control of the vehicle, based at least in part on a determination that the remote control authorization request message includes authentication data for the vehicle.

10. The system of claim 9, wherein the vehicle navigation system is configured to:

based at least in part authorization of the remote control system for remote driving control, transmit an authorization signal to the remote control system.

11. The system of claim 9, further comprising:

one or more interfaces configured to communicatively couple to a communication network, wherein the remote control request signal is transmitted to the remote control system via the communication network.

12. The system of claim 11, wherein the one or more interfaces comprises one or more cellular communication devices, wireless communication transceivers, radio communication interfaces, or any combination thereof.

13. The system of claim 9, wherein to authorize remote driving control of the vehicle, the vehicle navigation system is configured to:

identify an instance of identity data included in the remote control authorization request message; and determine that the instance of identity data matches a locally stored instance of identity data.

14. The system of claim 13, wherein, to authorize remote driving control of the vehicle, the vehicle navigation system is configured to:

transmit an authorization signal which specifies password information via which the remote control system can engage remote driving control of the vehicle; and execute one or more remote driving command signals received from the remote control system, based at least in part on a determination that the one or more remote driving command signals include the specified password information.

15. The system of claim 9, wherein the vehicle navigation system is configured to:

transmit a remote control request signal, to the remote control system, based at least in part upon user interaction with one or more user interfaces installed in the vehicle.

16. The system of claim 9, further comprising one or more sensors configured to collect sensor data for the vehicle, wherein the vehicle navigation system is further configured to:

determine the health state of the occupant based at least in part on the sensor data.

17. The system of claim 9, wherein the vehicle navigation system is configured to:

receive a disable remote driving control request;

navigate the vehicle to a stopped position; and enable manual driving control of the vehicle.

18. A non-transitory, computer-readable storage medium storing instructions that, when executed by one or more processors, cause the one or more processors to:

transmit a remote control request signal, to a remote control system, based at least in part upon a determination that an occupant of an interior of a vehicle is associated with a health state which meets at least one threshold;

receive a remote control authorization request message from the remote control system; and authorize the remote control system for remote driving control of the vehicle, based at least in part on a determination that the remote control authorization request message includes authentication data for the vehicle.

19. The non-transitory, computer-readable storage medium of claim 18, wherein the instructions further cause the one or more processors to:

identify an instance of identity data included in the remote control authorization request message; and determine that the instance of identity data matches a locally stored instance of identity data.

20. The non-transitory, computer-readable storage medium of claim 18, wherein the instructions further cause the one or more processors to:

authorize remote driving control of the vehicle concurrently with generating the remote control request signal, based at least in part upon the based at least in part upon user interaction with one or more user interfaces installed in the vehicle.

21. The non-transitory, computer-readable storage medium of claim 18, wherein the instructions further cause the one or more processors to:

selectively engage one or more sets of remote control devices based on one or more devices commands received from the remote control system, wherein the one or more sets of remote control devices are configured to provide externally-observable indications that the vehicle is being navigated via remote driving control.

* * * * *